(12) United States Patent
Allen et al.

(10) Patent No.: US 12,220,578 B2
(45) Date of Patent: Feb. 11, 2025

(54) ELECTRICAL APPARATUS AND METHODS FOR AN EYE

(71) Applicant: Centre for Eye Research Australia Ltd, East Melbourne (AU)

(72) Inventors: Penelope Jayne Allen, East Melbourne (AU); Chi Luu, East Melbourne (AU); David Anthony Xeiss Nayagam, East Melbourne (AU); Christopher Edward Williams, East Melbourne (AU); Owen Burns, East Melbourne (AU); Joel Villalobos, East Melbourne (AU)

(73) Assignee: Centre for Eye Research Australia Ltd, East Melbourne (AU)

( * ) Notice: Subject to any disclaimer, the term of this patent is extended or adjusted under 35 U.S.C. 154(b) by 628 days.

(21) Appl. No.: 17/436,289

(22) PCT Filed: Mar. 6, 2020

(86) PCT No.: PCT/AU2020/050212
§ 371 (c)(1),
(2) Date: Sep. 3, 2021

(87) PCT Pub. No.: WO2020/176947
PCT Pub. Date: Sep. 10, 2020

(65) Prior Publication Data
US 2022/0176123 A1    Jun. 9, 2022

(30) Foreign Application Priority Data

Mar. 6, 2019  (AU) .............................. 2019900738

(51) Int. Cl.
*A61N 1/36*    (2006.01)
*A61B 5/00*    (2006.01)
(Continued)

(52) U.S. Cl.
CPC ........ *A61N 1/36046* (2013.01); *A61B 5/0022* (2013.01); *A61B 5/398* (2021.01);
(Continued)

(58) Field of Classification Search
CPC .............. A61N 1/36046; A61N 1/0543; A61N 1/36167; A61N 1/37217; A61N 1/37247;
(Continued)

(56) References Cited

U.S. PATENT DOCUMENTS

2003/0014089 A1*  1/2003  Chow ................... A61F 9/0017
                                                    607/54
2004/0106965 A1*  6/2004  Chow .................. A61N 1/0543
                                                    607/54
(Continued)

FOREIGN PATENT DOCUMENTS

AU      2013202691 A1    5/2013
WO   WO-2011022773 A1    3/2011
(Continued)

OTHER PUBLICATIONS

Extended European Search Report issued in European Application No. 20765955.8, dated Oct. 26, 2022.
(Continued)

*Primary Examiner* — Eugene T Wu
(74) *Attorney, Agent, or Firm* — MARSHALL, GERSTEIN & BORUN LLP

(57) ABSTRACT

Disclosed is electrical stimulation apparatus and an associated method for delivering therapy to an eye of a patient is disclosed, the apparatus comprising: an implantable device comprising one or more electrodes for delivering therapeutic electrical stimulation to the eye, the implantable device being configured for implanting in a suprachoroidal space between the sclera and choroid layers of the eye. Also disclosed is electroretinography (ERG) apparatus for moni- (Continued)

toring an eye of a patient, the apparatus comprising: an implantable device comprising one or more electrodes for monitoring properties of the eye, the implantable device being configured for implanting in a suprachoroidal space between the sclera and choroid layers of the eye. Also disclosed are implantable devices, apparatuses and methods for the eye.

20 Claims, 23 Drawing Sheets

(51) Int. Cl.
  *A61B 5/398* (2021.01)
  *A61N 1/05* (2006.01)
  *A61N 1/372* (2006.01)

(52) U.S. Cl.
  CPC .......... *A61B 5/6821* (2013.01); *A61B 5/6837* (2013.01); *A61B 5/6839* (2013.01); *A61N 1/0543* (2013.01); *A61N 1/36167* (2013.01); *A61N 1/37217* (2013.01); *A61N 1/37247* (2013.01); *A61B 2562/043* (2013.01); *A61B 2562/046* (2013.01); *A61B 2562/164* (2013.01)

(58) Field of Classification Search
  CPC ...... A61N 1/375; A61B 5/0022; A61B 5/398; A61B 5/6821; A61B 5/6837; A61B 5/6839; A61B 2562/043; A61B 2562/046; A61B 2562/164; A61B 2560/04; A61B 5/065; A61B 2562/04; A61B 2562/222; A61B 2560/0271; A61B 2560/0276
  See application file for complete search history.

(56) References Cited

U.S. PATENT DOCUMENTS

| | | |
|---|---|---|
| 2010/0198299 A1 | 8/2010 | Shodo et al. |
| 2012/0245449 A1* | 9/2012 | Williams ........... A61N 1/36046 607/116 |
| 2014/0309613 A1 | 10/2014 | Behar-Cohen et al. |

FOREIGN PATENT DOCUMENTS

| | | |
|---|---|---|
| WO | WO-2013024437 A1 | 2/2013 |
| WO | WO-2017/210730 A1 | 12/2017 |

OTHER PUBLICATIONS

Shepherd et al., "Visual Prosthesis for the Blind", Trends in Biotechnology, vol. 31, No. 10, pp. 562-571, Oct. 2013.

Wong et al., "Efficacy of Supra-Choroidal, Bipolar, Electrical Stimulation in a Vision Prosthesis", 30th Annual International IEEE EMBS Conference, Vancouver, British Columbia, Canada, pp. 1789-1795, Aug. 20, 2008.

Cloherty et al., "Focal Activation of Primary Visual Cortex Following Supra-choroidal Electrical Stimulation of the Retina: Intrinsic Signal Imaging and Linear Model Analysis", 32nd Annual International Conference of the IEEE Embs, Buenes Aires, Argentina, pp. 6765-6768 Aug. 31, 20210.

International Search Report issued in PCT Patent Application No. PCT/AU2020/050212 mailed on Jun. 9, 2020.

Written Opinion issued in PCT Patent Application No. PCT/AU2020/050212 mailed on Jun. 9, 2020.

Nayagam et al., "Chronic Electrical Stimulation with a Suprachoroidal Retinal Prosthesis: A Preclinical Safety and Efficacy Study," *Plos One* (2014).

\* cited by examiner

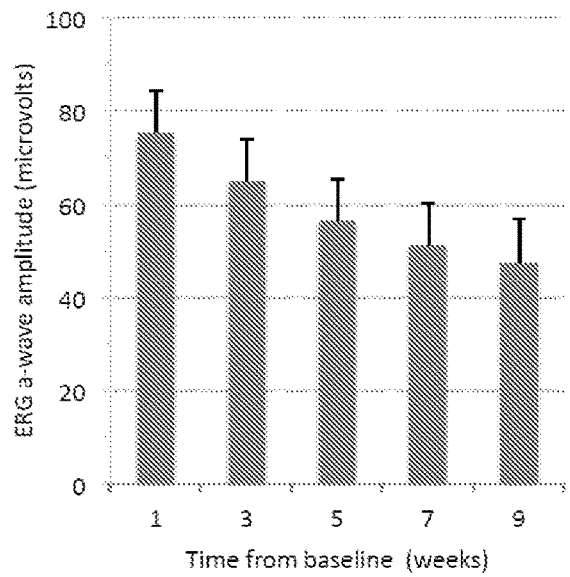
*Fig. 17*
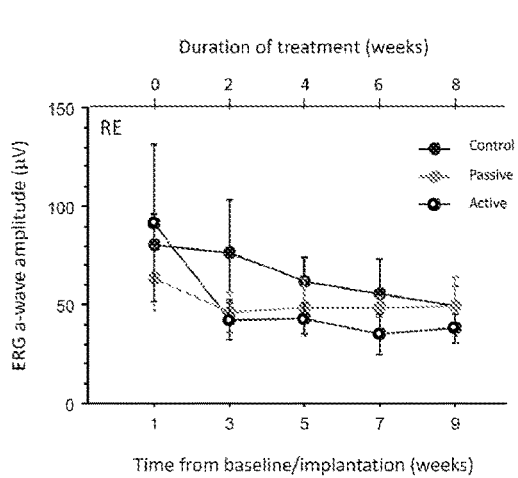
*Fig. 18a*
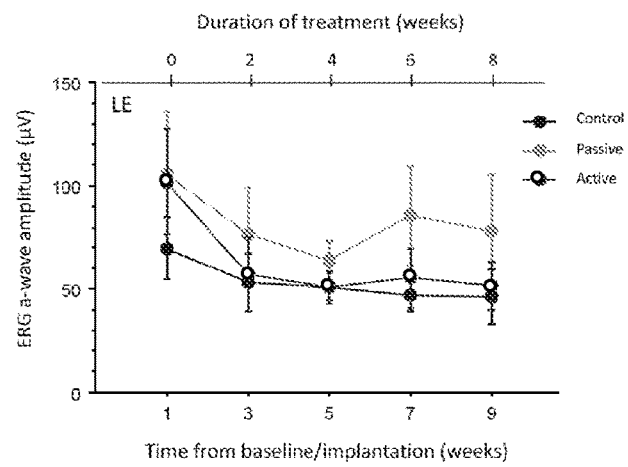
*Fig. 18b*
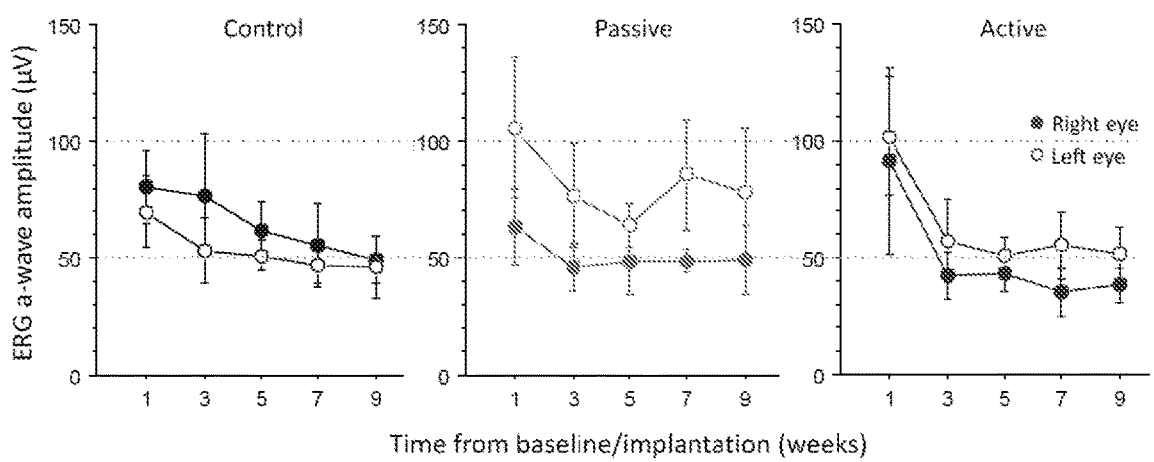
*Fig. 19a*  *Fig. 19b*  *Fig. 19c*

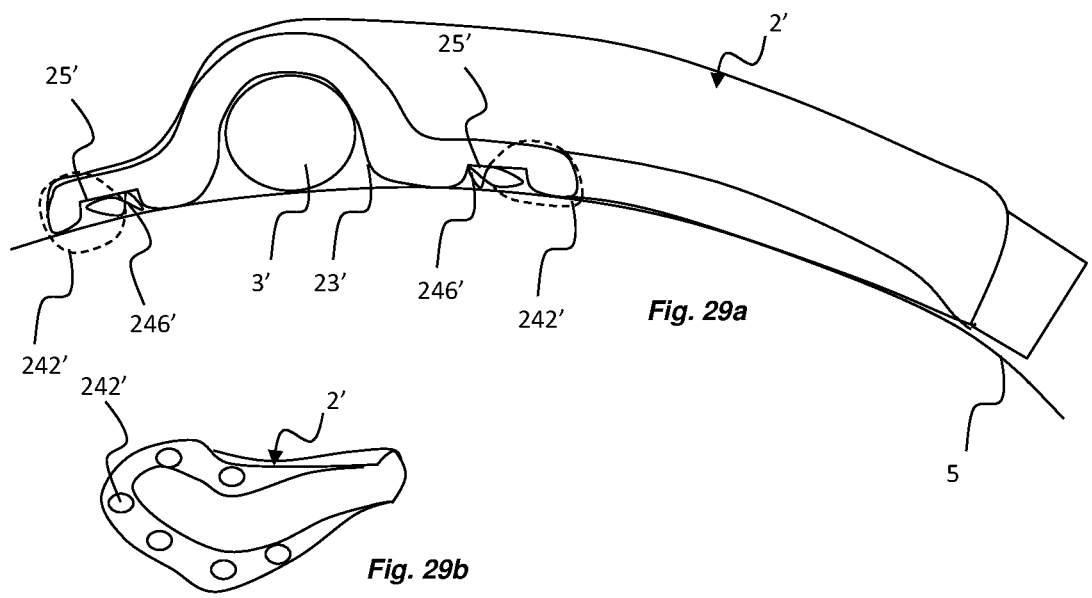
*Fig. 29a*
*Fig. 29b*
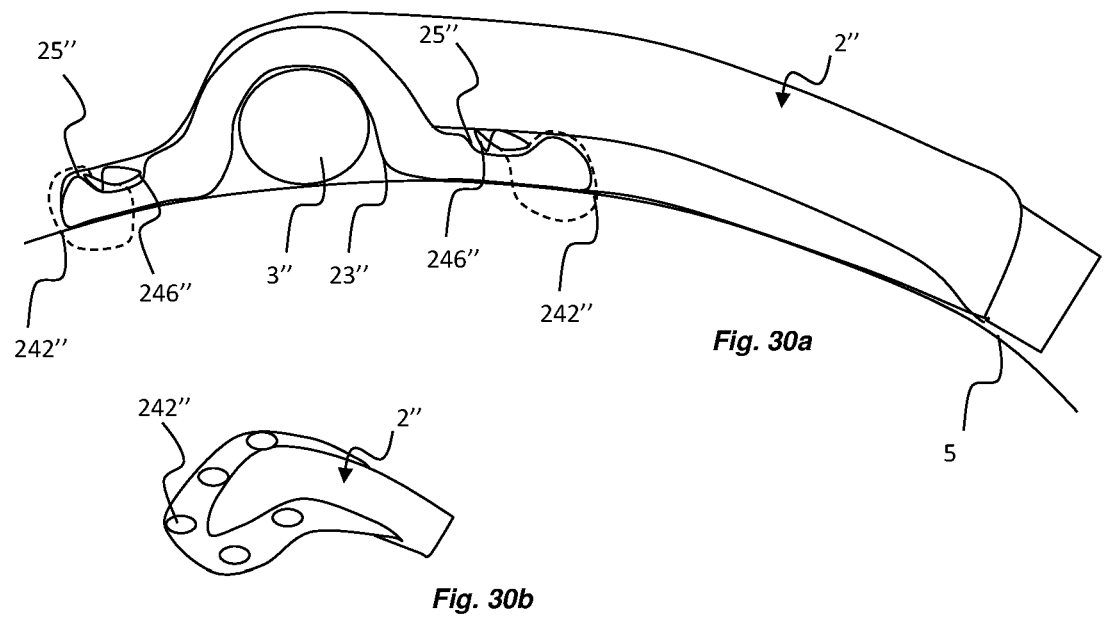
*Fig. 30a*
*Fig. 30b*

ELECTRICAL APPARATUS AND METHODS FOR AN EYE

CROSS-REFERENCE TO RELATED APPLICATION

This application claims priority to Australian provisional patent application no. 2019900738, filed 6 Mar. 2019, the entire contents of which is incorporated herein by reference.

TECHNICAL FIELD

The present patent application relates to apparatus and methods for electrically stimulating and/or monitoring electrical activity in an eye.

BACKGROUND

Electrical apparatus such as visual prostheses have been developed to restore vision within blind or partially blind patients. A visual prosthesis such as a retinal prosthesis commonly includes an implantable component having an electrode array, situated on or in a substrate, for placement in the eye on or near retinal nerve cells. Electrical signals are transmitted via the electrodes to the retinal nerve cells, triggering a perception of light within the patient's brain. The prosthesis can therefore provide the perception of vision to patients, e.g. whose retinal photoreceptors have become dysfunctional or lost.

Commonly, a visual prosthesis is used in conjunction with a video camera. A stream of images detected by the camera is converted into digital signals by an image processor and electrical signals are applied to the electrodes in accordance with the digital signals.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to one aspect of the present disclosure there is provided electrical stimulation apparatus for delivering therapy to an eye of a patient, the apparatus comprising:
  an implantable device comprising one or more electrodes for delivering therapeutic electrical stimulation to the eye, the implantable device being configured for implanting in a suprachoroidal space between the sclera and choroid layers of the eye.

According to another aspect, there is provided a method of delivering therapy to an eye of a patient, comprising:
  implanting an implantable device in a suprachoroidal space between the sclera and choroid layers of the eye; and
  delivering therapeutic electrical stimulation to the eye using one or more electrodes comprised in the implantable device.

The therapeutic electrical stimulation may provide for improvement of the visual function of the eye and/or prevent or slow degradation of the visual function of the eye (e.g. maintain visual function of the eye). Improvement of visual function may provide, for example, improvements in the patient's perception of any one or more of: brightness, contrast, spatial and/or temporal resolution, colours, shapes, movement and size of visual field. Similarly, the prevention or slowing down of degradation of the visual function may prevent or slow down degradation of, for example, the patient's perception of any one or more of: brightness, contrast, spatial and/or temporal resolution, colours, shapes, movement and size of visual field.

In general, therapeutic electrical stimulation can contrast with electrical stimulation that is intended solely to restore visual function by eliciting the perception of light as a direct result of the stimulation. In some embodiments, the therapeutic electrical stimulation may provide an improvement in visual function of the eye and/or prevent or slowing degradation of the visual function of the eye without eliciting a perception of light to the patient, or without eliciting a perception of light to that patient that is visually useful or intended to be visually useful.

The therapeutic stimulation may be provided as charge-balanced biphasic pulses. The pulses may have a square shape or otherwise.

In one embodiment, the therapeutic electric stimulation is provided at, for example, a current of about 50 to 150 μA and 0.5 to 200 pulses per second, for a session period of about 15 minutes to about 2 hours, 1 time to about 4 or about 5 times per week, for at least 3 weeks. In one embodiment, the therapeutic electrical stimulation is provided at a current of about 100 μA, 1 pulse per second, for 1 hour about 2 times per week, for at least 4 weeks. In one embodiment, the therapeutic electrical stimulation is provided at a current of between 50 to 150 μA, 200-500 microsecond per bi-phasic phase, at a rate of 50-150 biphasic pulses per second.

In one or more embodiments, the current is about 50 μA to about 150 μA, about 60 μA to about 150 μA, about 50 μA to about 140 μA, about 60 μA to about 140 μA, about 70 μA to about 140 μA, about 60 μA to about 130 μA, about 70 μA to about 130 μA, about 80 μA to about 130 μA, about 70 μA to about 120 μA, about 80 μA to about 120 μA, about 90 μA to about 120 μA, about 80 μA to about 110 μA, or about 90 μA to about 110 μA.

In one or more embodiments, the current has pulse rate of about 0.5 to about 200 pulses per second, about 1 to about 150 pulses per second, about 1 to about 50 pulses per second, about 50 to about 100 pulses per second, about 100 to about 150 pulses per second, about 50 to about 150 pulses per second, or about 75 to about 125 pulses per second.

In one or more embodiments, the current, charge and/or charge density of the therapeutic stimulation may be selected to be at a level that is between 0.5 to 2 times the current, charge and/or charge density that elicits the patient's visual perception (visual perceptual threshold). In one or more embodiments, the current, charge and/or charge density of the therapeutic stimulation may be selected to be at a level that is below a threshold at which a risk of an acute or chronic inflammatory response, histiocytic changes or morphological changes, to the eye, resulting from the stimulation, becomes unacceptable.

For example, in one or more embodiments, the charge delivered to the eye per electrode may be at least 20 nC, at least 30 nC, at least 40 nC, at least 50 nC, at least 60 nC, at least 70 nC, at least 80 nC, at least 90 nC, at 100 nC, at least 110 nC, at least 120 nC, at least 130 nC, at least 140 nC, or at least 150 nC, e.g. at a charge density of 7 to 50 μC·cm$^2$ and at about 50 pulses per second (or equivalent delivery of energy for different pulse rates). In one or more embodiments, the charge that is delivered to the eye per electrode may be no more than about 200 nC, about 250 nC or about 300 nC, e.g. at a charge density of about 90 μC·cm² and at about 50 pulses per second (or equivalent delivery of energy for different pulse rates).

In one or more embodiments, the current is delivered for a session of between about 15 minutes to about 2 hours, about 30 minutes to about 2 hours, about 15 minutes to about 105 minutes, about 30 minutes to about 105 minutes, about 45 minutes to about 105 minutes, about 30 minutes to about 90 minutes, about 45 minutes to about 90 minutes, or about 45 minutes to about 75 minutes.

In one or more embodiments, sessions are delivered for at least 1 time per week, at least 2 times per week, at least 3 times per week, at least 4 times per week, at least 5 times per week, 1 time to about 5 times per week; 1 time to about 4 times per week; 1 time to about 3 times per week; 1 time or about 2 times per week; about 2 to about 5 times per week; about 2 to about 4 times per week; about 2 to about 3 times per week; about 3 to about 5 times per week; about 3 to about 4 times per week; or about 4 to about 5 times per week. In one embodiment, sessions are delivered 1 time per week. In one embodiment, sessions are delivered about 2 times per week. In one embodiment, sessions are delivered about 3 times per week. In one embodiment, sessions are delivered about 4 times per week.

In one embodiment, sessions are delivered about 2 times per week with a minimum of three days and a maximum of four days between each session. In one embodiment, sessions are delivered about 3 times per week with a minimum of 2 days and a maximum of 3 days between each session. In one embodiment, sessions are delivered about 4 times per week with a minimum of 1 day and a maximum of 2 days between each session.

The therapeutic electrical stimulation may be administered substantially chronically. In one or more embodiments, the period of administration is about 3 weeks or more, about 4 weeks or more, about 5 weeks or more, about 6 weeks or more, about 2 months or more, about 4 months of more, about 6 months or more, about 1 year or more, or about 2 years or more.

Chronic electrical stimulation can have a neuroprotective effect on retinal cells. Positioning an implantable device that provides electrical stimulation suprachoroidally can provide an approach that is safe and stable and requires minimally-invasive surgery.

The therapeutic stimulation may protect against retinal cell loss in degenerative conditions, such as retinitis pigmentosa (RP), age-related macular degeneration (AMD) and glaucoma, or otherwise, including vascular and other conditions. The therapy may arrest retinal degeneration in the early stages of diseases, e.g. before a patient loses useful vision, or during intermediate or later stages of diseases.

In addition or as an alternative to providing therapeutic electrical stimulation of the eye, the implantable device may provide for monitoring of the eye, e.g. to monitor one or more properties of the eye for the purposes of disease monitoring or otherwise. For example, the implantable device may enable monitoring of electrically-evoked, or non-electrically-evoked, responses and the measurement of impedances both individually (on a per-electrode basis) or in a matrix (e.g. trans-impedances). This may be used to refine stimulation strategies in vivo and/or determine tissue response to the implant device. In general, monitoring of the eye, or monitoring of properties of the eye, as described herein, may include, for example, measuring of a signal at the eye, recording of signal data, processing of signal data and/or analysing of the signal data.

According to one aspect of the present disclosure there is provided electrical monitoring apparatus for monitoring an eye of a patient, the apparatus comprising:
    an implantable device comprising one or more electrodes for monitoring one or more properties of the eye, the implantable device being configured for implanting in a suprachoroidal space between the sclera and choroid layers of the eye.

According to another aspect, there is provided a method of monitoring an eye of a patient, comprising:
    implanting an implantable device in a suprachoroidal space between the sclera and choroid layers of the eye; and
    monitoring one or more properties of the eye using one or more electrodes comprised in the implantable device.

In any aspects described herein, the implantable device may comprise a substrate that the one or more electrodes are located in or on. The electrodes may be at least partly embedded in the substrate. The substrate may comprise a first, non-conductive material, e.g., a medical grade polymer material such as a silicone elastomer or polyurethane. Each electrode may comprise a second, conductive material such as a metal, e.g. a noble metal such as platinum. A portion of the substrate may provide a lip around a contact surface of each electrode. The lip may cover a peripheral edge of the contact surface and leave a central region of the contact surface exposed for making electrical contact, including electrochemical contact, with eye tissue. The lip may help anchor the electrode to the substrate.

The substrate may be an elongate substrate having a distal end, a proximal end, a first side, a second side, and first and second opposite surfaces each extending between the distal and proximal ends and the first and second sides. The electrodes may be at least partly embedded in the substrate and exposed at one or both of the first and second surfaces, e.g. the second surface, for making electrical contact with eye tissue. In some embodiments, the electrodes may be at least partly embedded in the substrate through forming of an initially flowable substrate material around the electrodes, prior to setting of the material. In some alternative embodiments, the electrodes may be positioned on the substrate, and embedded by way of a coating provided over the electrodes. Portions of the coating overlying the electrodes may be removed (e.g., by photolithography) to expose the underlying electrodes (or portions thereof) for making electrical contact with the eye tissue. The electrodes may be evenly distributed across the substrate or located generally closer to the distal end of the substrate than the proximal end. The substrate may be configured for insertion, via an incision, distal end first, to a stimulation and/or monitoring position between the sclera and choroid layers.

In any aspects described herein, the implantable device may be located at a temporal position of the eye. In some embodiments, the implantable device may be located at an inferior anterior temporal position of the eye. Alternatively, one or more parts of the implantable device may be located under one or both of the inferior and lateral rectus muscles of the eye. Alternatively, a part of the implantable device may be located between the inferior and lateral rectus muscles of the eye and a part of the implantable device may be located under one or both of the inferior and lateral rectus muscles of the eye. Alternatively, the implantable device may be located entirely under the inferior or lateral rectus muscle of the eye.

In one embodiment, the implantable device is configured to be located at an inferior anterior temporal position of the eye (e.g., in the inferior anterior temporal octant of the eye).

The proximal end of the implantable device may be located close to the limbus, e.g., less than 8 mm, less than 5 mm or less than 3 mm from the limbus.

In another embodiment, the implantable device is configured to be located underneath the lateral rectus muscle. The proximal end of the implantable device may again be located close to the limbus, e.g., less than 8 mm, less than 5 mm or less than 3 mm from the limbus.

In one embodiment, the implantable device is configured such that, when implanted, the distal-most electrodes are positioned beneath the retina, e.g., at the periphery of the retina and/or close to the central retina without infringing on the central retina. In some embodiments, the implantable device may be configured such that distance between the distal-most active electrode or electrodes and (i) the proximal end of the substrate, (ii) a point at which a lead extends from the substrate e.g. through an incision, and/or (iii) the limbus of the eye, is selected to facilitate this positioning. The distance between the distal-most active electrode or electrodes and the proximal end of the substrate may be between about 7 mm and 12 mm, 8 mm and 11 mm, 9 mm and 11 mm, or about 10 mm, for example. The distance between the distal-most active electrode or electrodes and the point at which a lead extends from the substrate e.g. through an incision, may be about 5 mm and 10 mm, 6 mm and 9 mm, 7 mm and 9 mm, or about 8 mm, for example. The distance between the distal-most active electrode or electrodes and the limbus of the eye may be about 10 mm and 15 mm, 11 mm and 14 mm, 12 mm and 14 mm, or about 13 mm, for example.

Certain positioning of the implantable device may enable space to be left in the eye for inclusion of a further implantable device configured to restore visual function through eliciting the perception of light as a direct result of the stimulation, e.g. a standard "bionic eye" device. In this regard, the implantable device may in some embodiments be kept away from a central retinal region where the bionic eye device may be located. Moreover, the positioning of the implantable device may correspond to superior visual field mapping area of the retina. Thus, to the extent that the device provides stimulation above a threshold level such as to levels that may elicit light perception, the stimulation may be less relevant and less obtrusive.

Conductors may be connected to each electrode. The conductors may extend through the substrate. One or more conductors may be provided to connect to each electrode. Where more than one conductor is present per electrode, redundancy may be provided in the device in case of failure of one or more of the conductors. Similarly, more electrodes than necessary may be provided for the sake of redundancy. The implantable device may comprise 2, 3, 4, 5 or more electrodes, for example. Where the implantable device provides for both electrical stimulation and electrical monitoring, at least two electrodes may be used for the stimulation and at least 2 electrodes may be used for the monitoring. Nevertheless, in some embodiments, the same electrodes may be used for stimulation and monitoring. In some embodiments, the one or more electrodes of the implantable device may comprise one or more active electrodes and one or more inactive electrodes. Nevertheless, in some embodiments, the implantable device may comprise active electrodes only, with one or more return electrodes being applied to the patient extraocularly, either as implanted electrodes or non-implanted electrodes. While the terms "active electrodes" and "inactive electrodes" have been used herein, it will be recognised that active electrodes may also be described as "recording electrodes", for example, and inactive electrodes may also be described as "return electrodes" or "reference electrodes", for example.

A lead may also be provided through which conductors connected to the electrodes extend from the implantable device. The lead may be configured to extend through an incision in the surface of the eye to enable electrical communication between the implantable device and an implantable electronics unit and/or between the implantable device and one or more external devices such as a processing device or controller. At the surface of the eye, the lead may be routed away from the eye. For example, the lead may be routed inferiorly or superiorly from the incision, at an angle relative to the a transverse anatomical plane of between about 5 to 30 degrees, 5 to 25 degrees, 10 to 25 degrees, 10 to 20 degrees or otherwise. For example, the angle may be about 20 degrees, about 15 degrees or about 20 degrees or otherwise. The lead may also be routed posteriorly from the incision. The lead may have a diameter of between about 0.5 mm to 1.5 mm, 0.5 mm and 1.3 mm, 0.7 mm and 1.3 mm, 0.7 mm and 1.1 mm or otherwise. For example, the lead may have a diameter of about 0.7 mm, 0.8 mm, 0.9 mm, 1.0 mm or 1.1 mm or otherwise. The lead may extend from the eye and be at least partially implanted at the side of the patient's head. For example, the lead may extend beneath tissue around the orbital bone of the patient and beneath tissue along the side of the patient's head (e.g. at or adjacent the zygomatic arch).

When an implantable electronics unit is employed, the electronics unit may comprise one or more of: an electrical stimulator for delivering electrical signals to the electrodes, an electrical amplifier for amplifying electrical signals received from the electrodes and/or a communications interface for communicating with an external processing device, controller and/or other external electrical system. Components of the electronics unit may be provided in an implantable housing, e.g. a 'can'. The housing may be a biocompatible metal housing, such as a titanium can. A return electrode may be connected to the electronics unit. The return electrode may be a wire or lead extending from the housing, or may be provided by conductive material of the housing itself.

The length of the substrate, in a longitudinal direction of the substrate extending between the distal and proximal ends of the substrate, may be between, for example, 5 mm and 15 mm, 5 mm and 13 mm, 7 mm and 13 mm, 7 mm and 11 mm, 7 mm and 12 mm, 9 mm and 11 mm, 9 mm and 12 mm, 10 mm and 12 mm, 11 mm and 12 mm, or otherwise. For example, the length may be about 7 mm, about 8 mm, about 9 mm, about 10 mm, about 11 mm, about 12 mm or otherwise. The width of the substrate, in a transverse direction of the substrate extending between the first and second sides of the substrate, may be between, for example, 3 mm and 7 mm, 3 mm and 6 mm, 4 mm and 6 mm, 4 mm and 5 mm, 5 mm and 7 mm or otherwise. For example, the width may be about 3.5 mm, about 4 mm, about 4.5 mm, about 5 mm, about 5.5 mm, about 6 mm, about 6.5 mm or otherwise. The electrodes may each have an exposed area of between, for example, 0.2 $mm^2$ and 7.1 $mm^2$, 0.8 $mm^2$ and 7.1 $mm^2$, 1.7 $mm^2$ and 7.1 $mm^2$, or 1.7 $mm^2$ and 4.9 $mm^2$ or otherwise. The electrodes may be disc-shaped electrodes with a circular periphery or otherwise. The diameter of the electrodes may be between, for example, 0.5 mm and 3 mm, 1 mm and 3 mm, 1.5 mm and 3 mm, 1.5 mm and 2.5 mm, or otherwise. For example, the diameter of the electrodes may be about 1 mm, about 1.5 mm, about 2 mm or about 2.5 mm, or otherwise. In one embodiment, the diameter of the electrodes is about 1.3 mm. Where a lip is provided around the periphery of the electrode, the lip may cover a diameter of between about 10% and 30%, e.g. about 25% of the electrode. For example, where the electrode has a diameter of about 1.3 mm, a portion of the electrode having a diameter of about 1 mm may be exposed only. The electrodes may all be the same size or may have different sizes. For example, the electrodes used for electrical stimulation may be smaller than electrodes used for monitoring. Each electrode may have an electrical, e.g., electrochemical, impedance that is less than 5 kΩ, providing a safe low charge density and diagnostic monitoring stability.

The electrodes may be sized and distributed to retain flexibility of the implantable device. For example, the electrodes may be positioned at either side of a longitudinal centre line of the substrate. No electrodes, or only a very small portion of one or more electrodes, may be positioned across the longitudinal centre line of the substrate. Thus, the substrate may easily flex at the longitudinal centre line, without being obstructed by stiffness of the electrodes. To enable no electrodes, or only a very small portion of the electrodes, to be positioned across the longitudinal centre line of the substrate, or to more generally retain flexibility of the substrate, the electrodes may have a diameter that is no more than half the width of the substrate. For example, when the substrate has a width of 4.5 mm, the electrodes may have a diameter of less than 2.25 mm, e.g. width diameters of about 2 mm.

To retain flexibility of the implantable device in the transverse or longitudinal directions, the electrodes may also be configured in a staggered pattern. For example, electrodes may be aligned in one or more rows extending longitudinally, but not aligned in any columns extending transversely, or electrodes may be aligned in one or more columns extending transversely, but not aligned in any rows extending longitudinally.

However, in alternative embodiments, electrodes may be aligned transversely and longitudinally and/or positioned across the longitudinal central line of the substrate, while still retaining a desired flexible configuration. In general, the size, shape and positioning of the electrodes may be controlled to ensure that the implantable device is stiff enough to be pushed through an incision (typically distal end first) and pushed between tissue layers of the eye without buckling or rolling up, yet flexible enough to adapt its shape to follow a curved path between the tissue layers, around the eye.

The conductors that extend from the one or more electrodes in the substrate, through the lead and/or other parts described herein, may have a helical configuration or a wavy shape. Accordingly, upon flexing of the apparatus, the conductors may expand or contract in length as necessary, avoiding damage to parts of the apparatus including the conductors themselves.

Electrical apparatus according to aspects or embodiments of the present disclosure may be used in electroretinography (ERG). ERG measures the electrical responses of various cell types in the retina, including the photoreceptors, bipolar cells, and the ganglion cells. Conventionally, electrodes are placed on the cornea or on the skin near the eye. However, electrical apparatus according to the present disclosure, in which one or more electrodes are located in an implantable device, may provide an improved or at least alternative approach to carrying out ERG.

Indeed, according to one aspect of the present disclosure there is provided electroretinography apparatus for monitoring an eye of a patient, the apparatus comprising:

an implantable device comprising one or more electrodes for monitoring properties of the eye, the implantable device being configured for implanting in a suprachoroidal space between the sclera and choroid layers of the eye.

According to another aspect, there is provided an electroretinography method comprising:

monitoring properties of the eye using one or more electrodes comprised in a device implanted in the eye in a suprachoroidal space between the sclera and choroid layers of the eye.

In some embodiments, properties of the eye that are measured may be in response to a stimulus such as a visual stimulation (e.g., flashes of light or pattern stimuli) or in response to electrical stimulation applied to the eye. In some embodiments, the apparatus may be connected to existing clinical ERG systems to perform ERG recording in clinics. In some embodiments, the apparatus may be connected to mobile ERG systems to perform ERG recording in clinics or other environments.

In some embodiments, the one or more electrodes of the implantable device may comprise one or more active electrodes and one or more inactive (return) electrodes. In alternative embodiments, the one or more electrodes of the implantable device may comprise one or more active electrodes, with one or more inactive electrodes being be provided at a separate implantable part of the apparatus, e.g. at an implantable electronics unit as described above. In alternative embodiments, the one or more electrodes of the implantable device may comprise one or more active electrodes, with one or more inactive (return) electrodes being applied externally to the patient. In some embodiments, the position of the active and inactive (return) electrodes as described above may be reversed.

Thus, the apparatus and method may enable ERG to be carried out without requiring any electrodes to be applied to external tissue of the eye, or, in some embodiments, without requiring any electrodes to be applied to any external tissue of the patient at all. This may be particularly advantageous if ERG testing is to be carried out in a non-clinical environment. Because electrodes are implanted, anaesthesia may not need to be applied at the eye during ERG testing. Still further, increased amplitude ERG recordings may be obtained due to the suprachoroidal positioning of the implantable device being closer to the retina. Moreover, the suprachoroidal positioning of the implantable device may be particularly stable and biocompatible, without being prone to causing wound erosion, e.g. in comparison to a subconjunctival positioning. Stability may be further enhanced when the implantable device is located under a muscle such as the lateral rectus muscle.

In any aspects and embodiments disclosed herein, where a lead is connected to the substrate, the lead may extend, as discussed, in an at least partially implanted manner, from the substrate, out of the eye, around the orbital bone and along a side of the patient's head, e.g. to an implantable electronics unit as described above. By providing one or more electrodes in an implanted device, and a lead that is at least partially implanted, particularly at a region adjacent the eye, a very stable electrode and lead configuration may be provided, ensuring that there is no substantial movement of the electrodes during a session of use and also no substantial movement of the electrodes from one session of use to another. For example, where the implantable device is to be used as part of ERG apparatus, the arrangement may ensure consistency between, and allow direct comparison between, the results of multiple sessions of ERG.

The electroretinography apparatus may include a processing device, which may be adapted to communicate with the implantable electronics unit. The electronics unit may be configured to amplify low level electrical signals sensed by the one or more electrodes before transfer of the signals to the processing device. The processing device may be worn by the patient, e.g., on the side of the patient's head, aligned with the implantable electronics unit. Transfer of the electrical signals from the implantable electronics unit to the processing device may be via a wireless connection, e.g. an RF connection. Transmitting and receiving RF coils may be employed in the electronics unit and processing device. The transfer of signals may be through tissue layers at the side of the patient's head.

The processing device may deliver the signals received from the implantable electronics unit to the ERG system, e.g. the clinical or mobile ERG system. The delivery may be via wires or wireless.

When a clinical ERG system is used, it may be a system that is known in the art, but which is typically intended to receive electrical signals from one or more electrodes located on a surface of the eye, rather than being implanted in the eye. ERG systems disclosed herein may be configured to control a stimulus to the implanted eye, e.g. a light or electrical stimulus. For example, the ERG system may include a controller to control a light, in order to provide for calibrated delivery of flashes in the field of view of the implanted eye. The light may be a hand-held light in some embodiments. The controller may also control, e.g. trigger, the recording of ERG signals (ERG response signals) using the implanted components through communication with the processing device.

When a mobile ERG system is used, the mobile ERG system may include eyewear, such as goggles, that is capable of delivering the stimulus to the implanted eye, e.g. light stimulus. The eyewear may be adapted to be worn over the eyes of the patient to cover the eyes (and part of the face) of the patient, placing the eyes in complete or almost complete darkness. When worn, the eyewear may define a dark inner chamber, located between inner walls of the eyewear and the patient's face and eyes. Accordingly, the eyewear may enable a patient to be dark-adapted for the purpose of ERG testing without necessarily requiring the patient to be located in a dark room.

The processing device may be integrated into or attached to the eyewear. For example the processing device may be positioned on a headband of the eyewear, where it may align with the implantable electronics unit.

The eyewear may include a light, e.g. an LED. The eyewear may include or be connected to a controller adapted to control flashing of the light. The light may be located in or adjacent to the internal chamber of the eyewear so that flashes of the light are presented within the internal chamber and therefore within the field of view of the patient's implanted eye. The controller may also control, e.g. trigger, the recording of ERG signals using the implanted components through communication with the processing device.

ERG system disclosed herein may include a mobile computing device, e.g. an app-based computing device such as a smartphone or tablet. The controller may be adapted to communicate, e.g. wirelessly, with the mobile computing device. In some embodiments, the controller may be at least partly comprised in the mobile computing device. The mobile computing device may be configured to present electroretinograms and/or associated data, to a user such as a clinician. The mobile computing device may include a display to display results of ERG testing. The mobile computing device may upload raw and processed data to a cloud database, e.g. via the internet. A server may be associated with the cloud database that performs further processing of the uploaded data. Clinicians or engineer may access the patient ERG data of the database via the server.

ERG systems disclosed herein, such as the mobile ERG system, may be particularly suited, for example, to home use or in clinics that do not have access to traditional, typically larger, ERG systems. This is made possible in part by use of electrodes that are pre-implanted in the eye, and do not need to be applied to the eye at the time of ERG testing. Therefore, lower-skilled clinicians may be employed to carry out the testing. Moreover, because the electrodes are implanted, when eyewear is used, the eyewear may be applied around the eyes of the patient without risk of disturbing the electrodes.

In some embodiments, ERG methods or apparatus according to embodiments of the present disclosure may take advantage of an occurrence that has been identified herein relating to the polarity of ERG response signals. In particular it has been identified that polarity of ERG response signals, recorded using one or more of the implanted electrodes, can change depending on the location of the electrodes in the patient's eye, including relating to the patient's retina. Methods and apparatus may be configured to determine the location, or a change in location, of the one or more electrodes based on the polarity of the one or more ERG response signals.

Indeed, in one aspect of the present disclosure there is provided electrode apparatus comprising:
  an implantable device for implanting in a patient's eye, the implantable device comprising one or more electrodes configured to measure one or more ERG response signals resulting from stimulus delivered to the eye;
  processing apparatus configured to determine the polarity of the one or more ERG response signals and determine the location, or a change in location, of the one or more electrodes based on the polarity of the one or more ERG response signals.

Moreover in one aspect, there is provided a method of determining the location, or a change in location, of one or more electrodes implanted in a patient's eye, the method comprising:
  delivering stimulus to the patient's eye;
  measuring an ERG response signal received at the one or more electrodes resulting from the stimulus;
  determining the location, or a change in location, of the one or more electrodes based on the polarity of the ERG response signal.

In some embodiments, a location of the one or more electrodes may be determined, e.g. using the processing device or otherwise, by:
  positioning the one or more electrodes at different locations in the eye;
  at each of the different locations, delivering stimulus to the patient's eye and measuring an ERG response signal received at the one or more electrodes resulting from the stimulus;
  identifying the polarities of the ERG response signals received at the different locations;
  identifying a difference between the polarities of the ERG response signals identified at two of the different locations; and
  determining a location of the one or more electrodes based on the difference in polarity occurring between the two of the different locations.

In some embodiments, the location where the polarity changes may be determined as a location beneath the retina of the patient's eye. In this regard, electrode locations to a side of the retina (e.g., beneath or anterior of the pars plana of the eye) may give rise to an ERG response signal having a first polarity, but when moved to an electrode location beneath the retina this may give rise to an opposite polarity of the ERG response signal.

In some embodiments, a change in location of the one or more electrodes may be determined, e.g. using the processing device or otherwise, by:
- delivering a first stimulus to the patient's eye;
- measuring a first ERG response signal received at the one or more electrodes resulting from the first stimulus;
- optionally delivering a second stimulus to the patient's eye;
- measuring a second ERG response signal received at the one or more electrodes resulting from the first or second stimulus;
- comparing the polarities of the first and second ERG response signals; and
- determining a change in location of the one or more electrodes if the identified polarity of the first ERG response signal is different from the identified polarity of the second ERG response signal.

In some embodiments, the change in the location of the one or more electrodes may be identified as a change from the one or more electrodes being located beneath the retina of the patient's eye to the one or more electrodes being located to a side of the retina (e.g., beneath or anterior of the pars plana of the eye), or vice-versa.

The methods and apparatus may be used in some embodiments to assist in a surgical procedure, e.g. to assist in identifying when the one or more electrodes have reached a desired location in the eye relative to the retina during implantation. In some embodiments, the location of the one or more electrodes may be determined substantially in real-time during a surgical procedure. Additionally or alternatively, in some embodiments the methods and apparatus may be used to identify if the one or more electrodes have moved, e.g. undesirably, from an intended implantable location relative to the retina. Such movement may occur over a period of time after initial surgical implantation.

In some embodiments, the determining of the location, or a change in location, of the one or more electrodes relative to the retina of the eye may also be based on amplitude of the ERG signal. When the amplitude is identified as relatively low or lower than amplitudes of other ERG signals, for example, it may be determined that the one or more electrodes are located at a position close to or closer to a threshold location for polarity inversion (the lower amplitude resulting from a vector-summation of different polarity amplitudes).

In some embodiments, the determining of the location or change in location of the electrodes may be used to determine the location or change in location of the implantable device that comprises the electrodes.

In some embodiments, the apparatus or method may provide an indication of the determined location or change in location, of the one or more electrodes (and/or of an implantable device that includes the one or more electrodes), to a user, e.g. through display of corresponding information on a display screen.

In aspects and embodiments disclosed herein, where a lead is connected to the substrate, the lead may comprise first and second lead sections that locate externally to the eye when the implantable device is in the implantation position. The second lead section may be configured to extend around an orbital bone adjacent the eye, and the first lead section may locate between the implantable device and the second lead section. The first lead section may have at least one pre-formed bend.

Indeed, according to one aspect of the present disclosure, there is provided electrical apparatus for stimulating and/or monitoring an eye of a patient, comprising:
- an implantable device comprising one or more electrodes, the implantable device being implantable at a stimulation and/or monitoring position between first and second tissue layers of the eye;
- a lead comprising one or more conductors connected to the electrodes, the lead extending outwardly from the implantable device;
- wherein the lead comprises first and second lead sections that locate externally to the eye when the implantable device is in the stimulation and/or monitoring position, the second lead section being configured to extend around an orbital bone adjacent the eye, and the first lead section being located between the implantable device and the second lead section;
- wherein the first lead section has at least one pre-formed bend.

The first and second tissue layers may be the sclera and the choroid in accordance with discussions above. However, the first and second tissue layers may be other layers, such as the choroid and the retina.

The at least one pre-formed bend may be a curved bend. The at least one pre-formed bend may provide a change in direction of the lead at the first lead section of at least 90 degrees, at least 120 degrees, at least 150 degrees or higher. The at least one pre-formed bend may provide a change in direction of about 180 degrees, for example. The at least one preformed bend may be a U-shaped bend, a double-U-shaped bend (e.g. an S-bend) or otherwise. The at least one pre-formed bend may be in only one plane or in more than one plane.

The at least one pre-formed bend may bend in a posterior direction when the implantable device is implanted in the eye. When the first lead section comprises a U-shaped bend, for example, the ends of the U-shape may therefore be located anteriorly of a middle-section, peak or apex of the U-shape.

The first lead section may be flexible and may have a length that is greater than the distance between the eye and the orbital bone. For example, the first lead section may have a length greater than the distance between a point, e.g. incision, of the eye at which the lead exits the eye, when the eye is in a forward-facing position, and a point on the orbital bone to which the lead makes contact.

During use of the electrical apparatus, the eye can rotate. To allow relatively unhindered rotation of the eye when the implantable device is implanted in the eye, the lead can exhibit a degree of flexibility and/or moveability. Without the flexibility and/or moveability of the lead, the lead can substantially hinder or prevent movement of the eye in one or more rotational directions. By providing, for example, a first lead section that is flexible and that has a length that is greater than the distance between the eye and the orbital bone, the eye may be able to move substantially in all rotational directions. As the eye rotates, depending on the direction of rotation, regions of the first lead section can bend and collect together or straighten and extend apart. By providing the first lead section with at least one pre-formed bend, the amount of force required to cause the lead to bend further or straighten can be significantly lower, reducing possible discomfort to the patient and/or possible eye damage.

The first lead section may have a circular cross-section or other cross-sectional shapes. The first lead section may have a smaller diameter than the second lead section or otherwise.

The one or more pre-formed bends of the first lead section may be formed during or subsequent to a moulding of the first lead section. The first lead section may comprise a plurality of conductive wires embedded in, or otherwise located within, a surrounding cladding layer. The cladding layer may be formed of medical grade silicone or other polymeric material, such as polyurethane, that is cured during the moulding process. The one or more bends may be formed by a post-curing technique. For example, at least one bend may be formed by rolling or holding the first lead section about a curved or angled surface while subjecting the first lead section to heating for a period of time. The curved or angled surface may be a cylindrical or part-cylindrical surface or otherwise. The radius of the curved surface may be at least 1.5 mm, at least 2 mm, at least 2.5 mm, at least 3 mm or otherwise. The pre-formed bend may have a corresponding radius of curvature. The heating may be conducted at a temperature of greater than 100° C., greater than 110° C., greater than 120° C., greater than 130° C. or otherwise. For example, heating may be conducted at a temperature of about 135° C. The heating may be conducted for a period of time greater than about 30 minutes, greater than 60 minutes, greater than 90 minutes, or otherwise. For example, heating may be conducted for a period of time of about 120 minutes.

The second lead section may comprise a reinforcement device that is adapted to be positioned at or adjacent an orbital bone. The reinforcement device may have a first end and a second end and may be elongated between the first end and the second end. The reinforcement device may be or provide a thickening of the second lead section. The reinforcement may be adapted to be positioned at or adjacent the orbital bone. The reinforcement device may be attached to the orbital bone. For example, the reinforcement device may be located in a notch formed in the orbital bone to assist with attachment to the orbital bone. The notch may include a recessed groove to receive the reinforcement device and an access opening through which the reinforcement device is locatable in the recessed groove. The access opening may be narrower than the recessed groove. The reinforcement device may be squeezed through the access opening into the recessed groove where it remains substantially trapped in position at the orbital bone.

The point at which the lead extends around the orbital bone, e.g. the point at which the notch is located, may be lower than a transverse plane extending through the centre of the eye. In a posterior direction, the notch (e.g. the groove) may be angled inferiorly or superiorly, e.g. by 15 degrees.

The reinforcement device may be formed integrally with the second lead section, e.g. by a moulding technique or otherwise, or may be a discrete component. For example, the reinforcement device may be clipped to and/or glued in position at the second lead section.

The second lead section, whether or not it is associated with a reinforcement device, can have at least one pre-formed bend. When a reinforcement device is provided, the reinforcement device may have a pre-formed bend, which creates the pre-formed bend of the second lead section when it is fixed in position at the second lead section. Nevertheless, the pre-formed bend at the second lead section may be formed using alternative techniques. For example, the pre-formed bend may be formed through a post-curing technique, e.g., in the same manner that the pre-formed bend at the first lead section is formed.

The at least one pre-formed bend of the second lead section may be configured to conform to and bend around the edge of the orbital bone (the orbital rim). The at least one pre-formed bend of the second lead section may have a sharper angle than the at least one pre-formed bend of the first lead section. For example, the at least one pre-formed of the first lead section may be a curved, U-shaped bend as discussed above, and the at least one pre-formed bend of the second lead section may be an angled, V-shaped bend.

When a single pre-formed bend is provided at the first lead section, and a single pre-formed bend is provided at the second lead section, the bends may in combination provide the lead with an S-shaped configuration or a 2-shaped configuration (i.e. it may be shaped substantially like the number 2). The bends at the first and second lead sections may therefore bend in opposite directions. The bend at the first lead section may bend in a posterior direction and the bend at the second lead section may bend in an anterior direction, for example.

The first lead section of the lead may comprise one or more stripes extending along at least a portion of the lead.

Indeed, according to one aspect, the present disclosure provides electrical apparatus for stimulating and/or monitoring an eye of a patient, comprising:
an implantable device comprising one or more electrodes, the implantable device being implantable at a stimulation and/or monitoring position between first and second tissue layers of the eye; and
a lead comprising one or more conductors connected to the electrodes, the lead extending outwardly from the implantable device;
wherein one or more stripes extend along at least a portion of the lead.

The one or more stripes may assist with placement of the lead during implantation of the stimulation device. Specifically, the one or more stripes may provide a visual indication to a surgeon implanting the stimulation device regarding whether or not the lead is twisted. Where the lead comprises first and second sections as described above, the one or more stripes may extend along at least the first lead section. In some embodiments the one or more stripes may extend along the entire length of the lead. The one or more stripes may be formed from a layer of titanium dioxide or other material that has a contrasting colour to adjacent parts of the lead. In some embodiments, two of the stripes may be provided, each stripe being located at substantially opposite sides of the lead.

As discussed above, implantable devices according to the present disclosure may comprise a substrate and one or more electrodes at least partially embedded in the substrate. The substrate may comprise a first, non-conductive material, and the at least one electrode comprising a second, conductive material. In some embodiments, one or more of the electrodes may comprise at least one aperture through which first material of the substrate at least partially extends to anchor the electrode to the substrate Indeed, according to one aspect of the present disclosure, there is provided an implantable device for stimulating and/or monitoring an eye of a patient, the implantable device comprising:
a substrate comprising a first, non-conductive material; and at least one electrode comprising a second, conductive material, the at least one electrode being at least partially embedded in the first material of the substrate and comprising at least one aperture through which first material of the substrate at least partially extends to anchor the electrode to the substrate.

The first, non-conductive material may be a flowable material that is set during a manufacturing process to form the substrate. While in a flowable state, and prior to setting, the first material may flow into the at least one aperture to completely or partially fill the aperture.

The first material may be a polymeric material that is set by curing. The first material may be a medical grade polymer material such as a silicone elastomer or polyurethane, for example. The second, conductive material may be a metal, e.g. a noble metal such as platinum.

In general, polymeric materials such as silicone elastomers or polyurethane used in substrates may not form a robust bond with noble metal materials used in electrodes. It has therefore been found that metal electrodes that are embedded at or close to the surface of elastomeric substrates can be prone to disengaging the substrates, e.g. 'popping out' of recesses in the substrates. By anchoring the electrode to the substrate in the manner described above, the risk of dislocation or popping out of the electrode can be substantially reduced.

The first material of the substrate may provide all of, or least the bulk of, the substrate. The portion of the first material that extends at least partially through the aperture of the electrode may be integral and homogenous with the first material forming all of, or the bulk of, the substrate.

The at least one aperture may be a bore hole in the electrode. The at least one aperture may have first and second opposite open ends. The first material may fill, e.g. completely fill, the aperture.

The first material may extend out of the aperture via the first and second ends. At one or both of the open ends, the first material may partially extend transversely to the aperture upon extending out of the aperture, e.g. across a surface of the electrode. The first material may form a continuous loop that extends through the aperture. The continuous loop may extend through the aperture and loop around a periphery of the electrode or through another aperture in the electrode.

By providing transversely extending portions of the first material and/or the continuous loop of first material, the at least one electrode may be trapped between portions of the first material, assisting in the anchoring of the electrode.

The at least one electrode may comprise a plurality of the apertures to increase anchoring strength.

The at least one electrode may be substantially flat. The electrode may have first and second opposite surfaces. The electrode may have a circular disk shape. The first surface of the electrode may face away from the substrate and may be at least partially exposed to enable electrical contact between the first surface and tissue of the eye. The second surface of the electrode may be buried within the substrate, e.g. the first material of the substrate.

The substrate may comprise a lip of the first material that extends around the periphery of the first surface of the electrode to assist with anchoring the electrode to the substrate, while leaving a region (e.g. a central region) of the first surface exposed.

The at least one aperture may extend between the first and second opposite surfaces of the electrode. The first open end of the aperture may be at the first surface of the electrode and the second open end of the aperture may be at the second surface of the electrode. The aperture may locate adjacent a peripheral edge of the electrode. For example, the at least one aperture may be positioned within the outer 33%, 25%, 15% or 10% of a diameter of the electrode. Where a plurality of the apertures are provided, each of the apertures may locate adjacent a peripheral edge of electrode. For example, each aperture may be positioned within the outer 33%, 25%, 15% or 10% of the diameter of the electrode. The apertures may be positioned in a ring pattern adjacent the peripheral edge of the electrode. The apertures may be uniformly spaced. By providing the apertures adjacent a peripheral edge of the electrode, the first, non-conductive material may extend through the electrode only at the peripheral edge of the electrode, ensuring that a central region of the first surface of the electrode remains exposed for electrical contact with tissue. Each aperture may have a diameter that is, e.g., less than 20%, less than 15% or less than 10% of the diameter of the electrode. For example, each aperture may have a diameter of between 100 µm and 800 µm. Each aperture may be circular, although other aperture shapes can be used.

Where a lip is provided, the first material may extend from the lip through the apertures at the periphery of electrode. The apertures may enhance the function of the lip as a means of assisting anchoring of the electrode to the substrate.

In addition to, or as an alternative to, providing one or more apertures that extend between the first and second opposite surfaces of the electrode, at least one aperture may be defined by a projection on the second surface of the electrode. First and second opposite ends of the aperture may be defined by the projection. The projection may be a loop, handle and/or hoop, the centre of which loop, handle and/or hoop provides the aperture. The projection may be formed by a strap. The projection may have a U-shape but, in combination with the second surface of the electrode, may provide a closed-loop. A plurality of projections, each defining at least one aperture, may be provided on the second surface of the electrode.

As discussed above, the second surface of the electrode may be buried within the substrate. By providing a projection at the second surface that defines the aperture, the first material of the substrate may extend through the aperture when the second surface is buried within the substrate during manufacturing of the device, e.g., while the first material of the substrate is in a flowable state as discussed above.

In apparatus of the present disclosure, an anchor device may be provided to anchor the lead at an outer surface of the eye, at or adjacent an opening in the eye, e.g. an incision, through which the lead extends. The anchor device may comprise a proximal end portion fixed to the lead and distal end portion connected to the proximal end portion. The anchor device may be releasably secured in a folded configuration. The anchor device may be adjustable from the folded configuration to an extended configuration Indeed, according to one aspect of the present disclosure there is provided electrical apparatus for stimulating and/or monitoring an eye of a patient, comprising:
an implantable device comprising one or more electrodes, the implantable device being implantable at a stimulation and/or monitoring position between first and second tissue layers of the eye; and
a lead comprising one or more conductors connected to the electrodes, the lead extending outwardly from the implantable device; and an anchor device to anchor the lead at an outer surface of the eye, at or adjacent an opening in the eye through which the lead extends, the anchor device comprising a proximal end portion fixed to the lead and a distal end portion connected to the proximal end portion, the anchor device being releasably secured in a folded configuration.

Moreover, in another aspect, there is provided a method of securing a lead at an outer surface of an eye of a patient, the lead being connected to an implantable device implanted at a stimulation and/or monitoring position between first and second tissue layers of the eye, the implantable device comprising one or more electrodes, the lead extending through an opening at an outer surface of the eye;

wherein an anchor device is provided comprising a proximal end portion fixed to the lead and a distal end portion connected to the proximal end portion, the anchor device being releasably secured in a folded configuration;

the method comprising adjusting the anchor device from the folded configuration to an extended configuration by releasing the securing of the anchor device.

In the folded configuration, the anchor device may be bent double, curved or curled back on itself or otherwise. The distal end portion (e.g. a distal tip thereof) may project towards the proximal end portion. On the other hand, in the extended configuration, the distal end portion (e.g. the distal tip thereof), may project away from the proximal end portion.

The anchor device may be releasably secured in the folded configuration by releasable securing of the distal end portion to the proximal end portion. The distal end portion may be releasably secured to the proximal end portion by one or more sutures, adhesive and/or other fixation means. To adjust the anchor device from the folded configuration to the extended configuration, a surgeon may release the securing of the distal end portion to the proximal end portion by e.g., cutting or undoing the one or more sutures and/or by applying a pull force to overcome the adhesion forces.

By releasably securing the anchor device in the folded configuration, the distal end portion of the anchor device may be temporarily held away from the opening (e.g., incision) in the outer surface of the eye through which the lead exits the eye. Accordingly, the distal end portion may not block or obstruct access to the opening in the outer surface of the eye. By maintaining such access to the opening, sutures may be applied relatively easily at the opening in the outer surface of the eye, e.g. to close up the incision, and/or other treatment to be applied at or adjacent the opening. Once such steps have been completed, the securing of the distal end portion to the proximal end portion can be released, whereupon the distal end portion may automatically, or through manipulation, project away from the proximal end portion. The distal end portion may then at least partly cover the opening in the outer surface of the eye. In general, the anchor device may extend over the lead and may cover at least part of, or all of, the opening in the outer surface of the eye. The distal and/or proximal end portions of the anchor device may be secured to the outer surface of the eye using one or more sutures or other fixation means. In some embodiments, the proximal end portion may be secured to the outer surface of the eye prior to the release from the folded configuration.

In any aspects disclosed herein, when secured to the outer surface of the eye, the anchor device may provide support and stabilisation for the lead as it extends out of the opening in the outer surface of the eye. Furthermore, the anchor device may shield the opening in the outer surface of the eye. The anchor device may also serve to route the lead in an appropriate direction away from the anchor device and the eye, e.g., past extraocular muscles of the eye and towards the lateral orbital rim. To achieve this routing, the anchor device may cause the lead to follow, or assist the lead in following, a bent path. The lead may bend by, for example, 45 to 135 degrees at the anchor device. In one embodiment, the bend of the lead at the anchor device may be a substantially right-angled bend (90 degree bend). In another embodiment, the bend may be about 50 to 70 degrees, e.g. about 55 or about 60 degrees.

The anchor device may be substantially flexible. The anchor device may comprise a polymeric material such a medical grade silicone or polyurethane. The anchor device may comprise a stiffening element embedded therein such as a mesh, e.g. polyethylene terephthalate mesh (Dacron™ mesh). The anchor device may be in the form of a patch or flap. The anchor device may be planar. The anchor device may have a pre-formed shape, e.g. channel or recess, that is adapted to receive a portion of the lead when it secures the lead to the outer surface of the eye and/or to receive one or more suture knots, preventing the knots from applying pressure to or rubbing of the anchor device. For example, the anchor device may have one or more pre-formed suture knot recesses, separate to a channel or recess adapted to receive a portion of the lead. Each suture knot recess may be adapted to receive one or more respective suture knots. One or more suture knot recesses may be provided as a depressed portion on a top surface of the anchor device. Additionally or alternatively, one or more suture knot recesses may be provided on an underside of the anchor device to create a pocket between the anchor device and the outer surface of the eye. In some embodiments, suture knot recesses may be provided on both the top surface and the underside of the anchor device. During surgery, after a suture knot has been tied, the suture may be rotated to position the knot in a recess.

In aspects and embodiments of the present disclosure, the substrate of the implantable device may have a first surface that is curved and the degree of curvature of the first surface may increase in the longitudinal direction of the substrate from a central region of the substrate at least towards the distal end of the substrate. Moreover, in the width direction of the substrate, the first surface may be curved and the degree of curvature of the first surface may increase in the width direction from a central region of the substrate at least towards one of the first and second sides of the substrate.

Indeed, according to one aspect of the present disclosure, there is provided an implantable device for stimulating and/or monitoring an eye of a patient, the implantable device comprising:

an elongate substrate having a distal end, a proximal end, a first side, a second side, a first surface and a second surface, the first and second surfaces each extending on opposite sides of the substrate between the distal and proximal ends and the first and second sides, a longitudinal direction of the substrate extending between the distal and proximal ends of the substrate and a width direction of the substrate extending between the first and second sides of the substrate;

one or more electrodes located at or adjacent the distal end of the substrate;

wherein the distal end of the substrate is configured for insertion, via an incision, to a stimulation and/or monitoring position between first and second tissue layers of the eye; and wherein:

in the longitudinal direction of the substrate, the first surface is curved and the degree of curvature of the first surface increases in the longitudinal direction from a central region of the substrate at least towards the distal end of the substrate; and/or in the width direction of the substrate, the first surface is curved and the degree of curvature of the first surface increases in the width direction from a central region of the substrate at least towards one of the first and second sides of the substrate.

In one embodiment, the degree of curvature of the first surface increases in the longitudinal direction from the central region of the substrate towards both the distal and proximal ends of the substrate.

In one embodiment, the degree of curvature of the first surface increases in the width direction from the central region of the substrate towards both the first and second sides of the substrate.

The increase in curvature may be a continuous increase in curvature or a stepped increase in curvature. For example, the first surface in the longitudinal direction and/or the width direction may have different regions, each region having a constant radius of curvature, but with the radius of curvature changing from one region to the next.

The curvature at any one or more of the curved regions of the substrate may be part-spherical. The curvature at the central region of the substrate may be part-spherical and may substantially follow the spherical curvature of the eye.

The first and second tissue layers may be the sclera and the choroid of the eye, respectively. The first surface may be configured to lie against the inside of the sclera layer. The relatively low curvature of the first surface at the central region may reduce the amount of static pressure against the sclera. Nevertheless, the relatively high curvature of the first surface towards the ends and/or sides of the substrate may assist in the insertion of the substrate between the first and second tissue layers of the eye. The substrate may be pushed into place between the first and second tissue layers, causing separation of the first and second tissue layers. The relatively high curvature may assist in separating the first and second tissue layers. In general, the curvature of the substrate may ease surgical placement and forces. Moreover, the curvature may help support the incision in the eye through which the implantable device is implanted in the eye.

The curvature of the substrate may be such that the substrate tapers in thickness from a central region towards the ends and/or sides of the substrate. In general, in any aspects and embodiments disclosed herein, the substrate may taper in thickness from a central region towards the ends and/or sides of the substrate.

Where implantable devices of the present disclosure include a plurality of electrodes used to electrically stimulate the eye, in some embodiments electrical current may be applied to a plurality of the electrodes simultaneously. For example, the electrodes may be configured in an array that includes one or more groups of electrodes, e.g. electrodes grouped in lines or grouped in other arrangements. Electrical current may be applied simultaneously to electrodes of the group. The group of electrodes may include at least 2 electrodes, at least 3 electrodes or at least 4 electrodes, for example. The electrodes of the group may be electrically addressed in parallel or may be ganged together.

The simultaneous addressing of electrodes may provide an increased penetration of the electric field in eye tissue, leading to better efficacy. Moreover, reduced power consumption may be achieved as a result of lower impedances and lower charge required per electrode.

In any of the aspects described herein, the substrate of the implantable device may include one or more navigation markers to assist in the implantation of the implantable device. The navigation markers can serve as an indicator of the depth of insertion of the implantable device through an incision in the eye and/or as an indicator of the orientation of the implantable device relative to the incision.

Indeed, according to one aspect of the present disclosure, there is provided an implantable device for stimulating and/or monitoring an eye of a patient, the implantable device comprising:

an elongate substrate having a distal end, a proximal end, a first side, a second side, a first surface and a second surface, the first and second surfaces each extending on opposite sides of the substrate between the distal and proximal ends and the first and second sides, a longitudinal direction of the substrate extending between the distal and proximal ends of the substrate and a width direction of the substrate extending between the first and second sides of the substrate;

one or more electrodes located at or adjacent the distal end of the substrate;

wherein the distal end of the substrate is configured for insertion, via an incision, to a stimulation and/or monitoring position between first and second tissue layers of the eye; and wherein:

the substrate comprises one or more navigation markers, each navigation marker providing at least one of (i) an indication of the depth of insertion of the implantable device through the incision and (ii) an indication of the orientation of the implantable device relative to the incision.

At least one of the navigation markers may be a line. The line may be printed on the substrate. Alternatively, the line may be etched or moulded into the substrate, for example. The line may be provided on the first or second surface of the substrate. The line may be a straight line. The line may extend in the width direction of the substrate, perpendicular to the longitudinal direction of the substrate.

A first one of the navigation markers may be provided to mark the position at which the implantable device, when fully implanted, is to align with the incision in the eye. The first marker when positioned at the incision may indicate that the implantable device has been inserted to the full implantation depth through the incision. The first marker when positioned at the incision may indicate the orientation of the implantable device relative to the incision at the full implantation depth. Appropriate orientation at the full implantation depth may be when the first marker is positioned directly underneath and extends parallel to the incision.

A second one of the navigation markers may be provided to indicate that the implantable device has been inserted to a predetermined intermediate implantation depth through the incision, e.g. at least half of the full implantation depth. The second navigation marker may be located distally of the first navigation marker (if the first navigation marker is also present). The second marker when positioned at the incision may indicate that the implantable device has been inserted to the intermediate implantation depth through the incision. The second marker when positioned at the incision may indicate the orientation of the implantable device relative to the incision at the intermediate implantation depth. Appropriate orientation at the intermediate implantation depth may be when the second marker is positioned directly underneath and extends parallel to the incision.

Additional markers, e.g. lines, may be provided to provide additional indications of the depth of insertion of the implantable device and/or to ensure suitable orientation of the implantable device at those different depths.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the accompanying Figures in which:

FIGS. 8a, 8b and 8c, show top, oblique and side views, respectively, of an alternative electrode for use in an implantable device according to an embodiment of the present disclosure;

FIGS. 9a, 9b and 9c, show top, oblique and side views, respectively, of another alternative electrode for use in an implantable device according to an embodiment of the present disclosure;

FIG. 17 shows, for a second example study, a bar graph of ERG a-wave amplitude, at different time points, from control group animals that did not undergo surgery or receive electrical stimulation treatment;

FIGS. 18a and 18b show, for the second example study, and for right eyes (RE) and left eyes (LE), respectively, line graphs of ERG a-wave amplitude at different time points, for active, passive and control group animals, wherein the right eyes included an actively stimulated implanted electrode device (active group animals), or a passively (non-)stimulated implanted (sham) electrode device (passive group animals), or no implanted electrode device (control animals), and wherein the left eyes had no implanted electrode device (active, passive and control group animals);

FIGS. 19a, 19b and 19c show, for the second example study, and the control, passive and active groups, respectively, line graphs of ERG a-wave amplitude at different time points for the right and left eyes;

FIGS. 29a and 29b show, respectively, a cross-sectional view and an oblique bottom view of an anchor device according to an embodiment of the present disclosure;

FIGS. 30a and 30b show, respectively, a cross-sectional view and an oblique top view of an anchor device according to another embodiment of the present disclosure.

DETAILED DESCRIPTION OF EMBODIMENTS

Embodiments of the present disclosure relate to electrical apparatus for applying therapeutic electrical stimulation to any eye of a patient and/or monitoring the eye of the patient.

Figure 1:
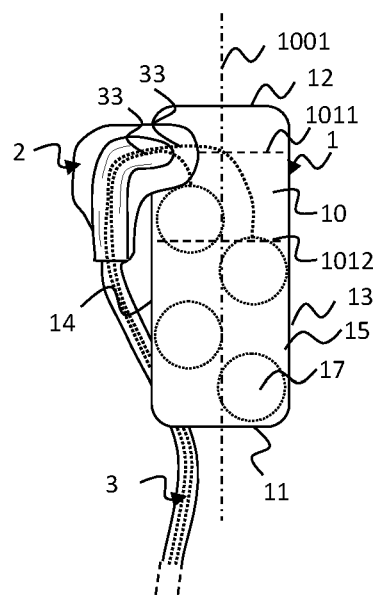
FIG. 1 shows a top view of electrical apparatus, including an implantable device for implanting in an eye, a lead and an anchor device, according to an embodiment of the present disclosure.

FIG. 1 shows a top view of electrical apparatus according to an embodiment of the present disclosure, the apparatus including an implantable device 1, an anchor device 2 and a lead 3.

The implantable device has a flexible substrate 10 with a distal end 11, a proximal end 12, a first side 13, and a second side 14. The substrate 10, when viewed from above, is substantially rectangular, with curved corners to minimise surgical trauma. The longitudinal direction (length) of the substrate extends between the distal and proximal ends 11, 12 and the transverse direction (width) of the substrate extends between the first and second sides 13, 14. The substrate 10 includes first and second opposite surfaces 15, 16 that each extend between the distal and proximal ends 11, 12 and between the first and second sides 13, 14 (see also FIG. 3a). Electrodes 17 are partially embedded in the substrate, which electrodes 17 are used to apply electrical current to tissue of the eye for the purposes of therapeutic electrical stimulation and/or are used to monitor properties of the eye by receiving electrical current from tissue of the eye. In this embodiment, four electrodes 17 are provided, the electrodes being arranged in a staggered pattern with electrodes 17 aligned in rows extending in the longitudinal direction of the substrate but offset in the transverse direction of the substrate. The electrodes 17 are exposed at the second surface 16 of the substrate.

The length of the substrate 10 is between about 9 mm and 11 mm, e.g. about 10 mm, although other lengths are possible. The width of the substrate 10 is between about 4 and 5 mm, e.g. about 4.5 mm, although other widths are possible. The electrodes 17 are disc-shaped electrodes with circular peripheries, although other shapes are possible. The diameters of the electrodes 17 are between about 1.5 mm and 2.5 mm, e.g., about 2 mm and have an area of between about 1.8 mm$^2$ and about 4.9 mm$^2$, e.g., about 3.1 mm$^2$. However, as discussed in more detail below, a lip 101 surrounds the electrodes 17 such that only a portion of each electrode, having a diameter of about 1.5 mm (and an area of about 1.8 mm$^2$), is exposed from the substrate, although other diameters are possible.

In addition to covering a relatively large area of the substrate 10, the electrodes 17 are sized and distributed to retain flexibility of the implantable device 1. The electrodes 17 are positioned substantially at either side of a longitudinal centre line 1001 of the substrate 10. No major part of any electrode 17 is this embodiment is positioned across the longitudinal centre line 1001 of the substrate 10. Thus, the substrate 10 can easily flex at the longitudinal centre line 1001, without being substantially hindered by any electrode stiffness. So that it possible to avoid positioning the electrodes 17 across the longitudinal centre line 1001 of the substrate 10, electrodes 17 are provided each having a diameter that is less than half the width of the substrate 10. Each electrode also has an impedance that is less than 5 kΩ, providing for safe low charge density stimulation as well as diagnostic monitoring stability. However, electrode impedances may be used in the range of ~2-20 kΩ, for example.

Each electrode 17 is connected to one or more separate electrical conductors 33, e.g., a biocompatible metal wires such as a platinum wires. The conductors 33 extend through the substrate, and extend out of the substrate and through the lead 3. Although only a basic representation of the conductors 33 is provided in FIG. 1, in practice the conductors 33 may be configured in a curved and/or helical configuration, enabling the conductors to adjust to flexing of the implantable device 1 and/or lead 3.

The substrate 10 of the implantable device includes one or more navigation markers 1011, 1012 to assist in the implantation of the implantable device 1. The navigation markers 1011, 1012 can serve as an indicator of the depth of insertion of the implantable device 1 through an incision in the eye and/or as an indicator of the orientation of the implantable device 1 relative to the incision. In this embodiment, at least two navigation markers 1011, 1012 are provided, each on the first (rear) surface 15 of the substrate 10. In this embodiment, the navigation markers 1011, 1012 are provided in the form of lines. The lines are printed on the rear surface 15 of the substrate 10, although in alternative embodiments they may be etched or moulded into the substrate, for example. The lines 15 are straight lines that extend in a transverse (width) direction of the substrate 10, perpendicularly to the longitudinal (length) direction of the substrate 10.

A first one of the navigation markers 1011 is provided to mark the position at which the implantable device 1, when fully implanted, is to align with the incision in the eye. The first marker 1011 when positioned at the incision not only indicates that the implantable device 1 has been inserted to the full implantation depth through the incision, but also provides a means of ensuring that the implantable device 1 is oriented appropriately relative to the incision at the full implantation depth. In this embodiment, appropriate orientation at the full implantation depth is achieved when the first marker is positioned directly underneath and extends parallel to the incision. Notably, the first marker is positioned slightly distally of the proximal end of the substrate 10, since the implantable device 1, when fully implanted, is configured to extend either side of the incision. A major portion (distal side) of the implantable device 1 is to be located to one side of the incision with a remaining minor portion (proximal side) of the implantable device 1 being tucked to the opposite side of the incision (see e.g. FIGS. 6a to 6c). The lead 3 extends from the implantable device 1 at a position that is aligned with the first marker 1011, since it is arranged to extend from the implantable device 1 immediately through the incision.

A second one of the navigation markers 1012, which is located distally of the first navigation marker, provides an intermediate marker. It provides an indication, for example, that the implantable device 1 has been inserted to a predetermined intermediate implantation depth through the incision, e.g. at least half of the full implantation depth. Moreover, it provides an indication that the implantable device 1 is being inserted at the appropriate orientation relative to the incision at the intermediate implantation depth. In this embodiment, appropriate orientation is achieved at the intermediate implantation depth when the second marker 1012 is positioned directly underneath and extends parallel to the incision. Additional markers, e.g. lines, may be provided to provide additional indications of the depth of insertion of the implantable device and/or to ensure suitable orientation of the implantable device 1 at those different depths.

Figure 2A:
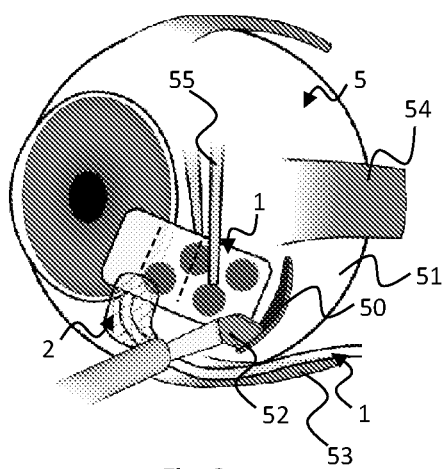
FIGS. 2a and 2b illustrate implanting of the implantable device of FIG. 1 in an eye.
Figure 2B:
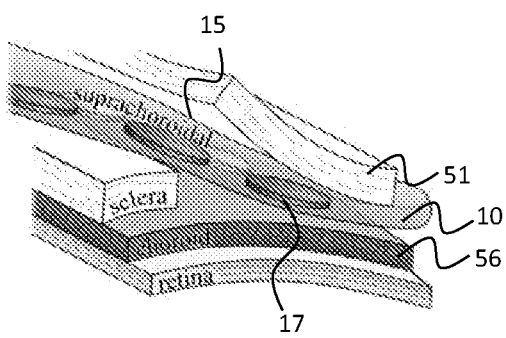

An example method of implanting the implantable device 1 in an eye 5 is now discussed with respect to FIGS. 2a and 2b. An incision 50 is made in the sclera 51 of the eye 5 with a scalpel 52, the incision 50 being slightly wider than the width of the substrate 10 of the implantable device 1. For example, the incision may have a width of about 5 mm. The incision 50 is made between the inferior rectus muscle 53 and the lateral rectus muscle 54 of the eye 5. The incision is positioned about 4 to 5 mm posterior from the intramuscular septum. The distal end 11 of the substrate 10 is pushed into the incision 50, using soft-tipped forceps 53, through the sclera 51 and into a pocket between the sclera 51 and the choroid 56 (See FIG. 2b). During the insertion process, the first and second markers 1011, 1012 provide indications of insertion depth. During the insertion process, a check is made to ensure that the second marker 1012 is aligned with the incision 50 as it passes through the incision and a correction of the orientation is made if necessary. Once the implantable device is fully inserted at the correct orientation, which is confirmed by alignment of the first marker 1011 with the incision 50, the opening of the incision 50 is closed using sutures. When implanted, the implantable device 1 of the present embodiment is located entirely between the inferior and lateral rectus muscles 53, 54 of the eye 5, in an inferior anterior temporal position of the eye (e.g., in the inferior anterior temporal octant of the eye). In alternative embodiments, a part of the implantable device may be located between the inferior and lateral rectus muscles of the eye and a part of the implantable device may be located under one or both of the inferior and lateral rectus muscles of the eye. In alternative embodiments, the incision and/or all or part of the implantable device may be located under the lateral rectus muscle.

Therapeutic stimulation provided by the implanted device 1, through delivery of electrical current from its electrodes 17 to surrounding tissue of the eye, can provide for improvement of the visual function of the eye and/or prevent or slow degradation of the visual function of the eye. Improvement of visual function can provide, for example, improvements in the patient's perception of any one or more of: brightness, contrast, resolution, colours, shapes, movement and size of visual field. Similarly, the prevention or slowing down of degradation of the visual function can prevent or slow down degradation of, for example, the patient's perception of any one or more of: brightness, contrast, resolution, colours, shapes, movement and size of visual field.

In general, this therapeutic stimulation can contrast with stimulation that is intended solely to restore visual function through eliciting the perception of light as a direct result of the stimulation. The therapeutic stimulation may provide an improvement in visual function of the eye and/or prevent or slowing degradation of the visual function of the eye without eliciting a perception of light to the patient, or without eliciting a perception of light to that patient that is visually useful or intended to be visually useful. Additionally or alternatively, the therapeutic stimulation can provide an improvement in visual function of the eye and/or prevent or slowing degradation of the visual function of the eye at a portion of the eye that is not in contact with the electrodes delivering the electrical stimulation.

The therapeutic stimulation may protect against retinal cell loss in degenerative conditions, such as retinitis pigmentosa (RP), age-related macular degeneration (AMD) and glaucoma or otherwise, including vascular and other conditions. The therapy may arrest retinal degeneration in the early stages of diseases, e.g. before a patient loses useful vision, or during intermediate or later stages of diseases. Chronic electrical stimulation can have a neuroprotective effect on retinal cells.

By implanting the implantable device 1 suprachoroidally and at an inferior anterior temporal position of the eye (e.g., in the inferior anterior temporal octant of the eye) or elsewhere, efficacious stimulation and/or monitoring of tissue of the eye can be achieved. Positioning of the implantable device 1 suprachoroidally can provide an approach that is safe and stable and requires minimally-invasive surgery. Moreover, the positioning of the implantable device 1 in the inferior anterior temporal octant can ensure that appropriate space is left in the eye for implantation of a further implantable device, such as a device configured to restore visual function through eliciting the perception of light as a direct result of the stimulation, e.g. a standard "bionic eye" device. In this regard, the implantable device may be kept away from a central retinal region where the bionic eye device may be located. Moreover, the positioning of the implantable device can correspond to a superior visual field mapping area of the retina. Thus, to the extent that it provides stimulation above a threshold level such as to elicits light perception, the stimulation may be less relevant to sight and less obtrusive. Still further, the positioning of the implantable device in the inferior part of the eye can ensure that any bleeding associated with surgery would drain downwards, away from the central retina, and not flow over the central retina.

In addition or as an alternative to providing therapeutic electrical stimulation, the implantable device 1 may be used to monitor properties, such as voltages, impedances or otherwise, of the eye. In one embodiment, the implantable device 1 is used to perform electroretinography monitoring (ERG).

In addition to the positioning of the implantable device 1 in the eye, safety, stability and the need for only minimally invasive surgery is provided in part through the shaping of the substrate 10 of the implantable device. A side view, an end view and an oblique view of the substrate 10 are provided in FIGS. 3a, 3b and 3c, respectively. As can be seen, the first surface 15 of the substrate is curved. When positioned suprachoroidally, the first surface 15 is designed to rest against the inner surface of the sclera 51, as illustrated in FIG. 2b.

Figure 3A:
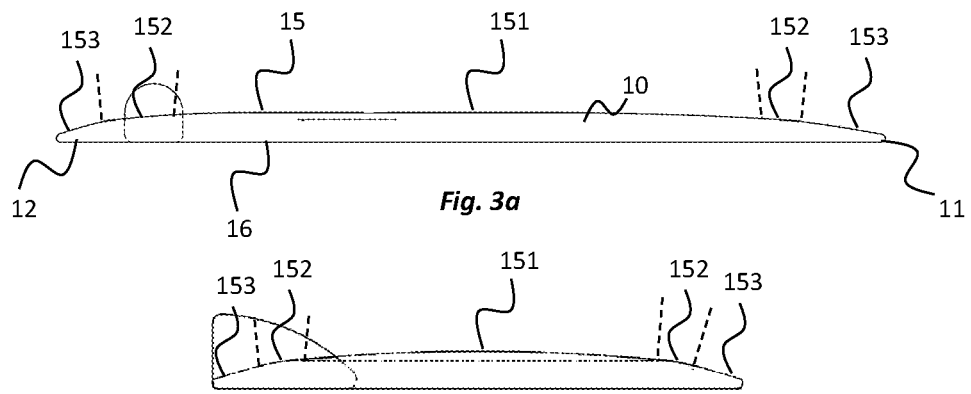
FIGS. 3a, 3b and 3c show side, end and perspective views, respectively, of the substrate of the implantable device of FIG. 1.
Figure 3B:
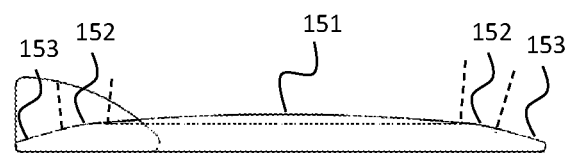
Figure 3C:
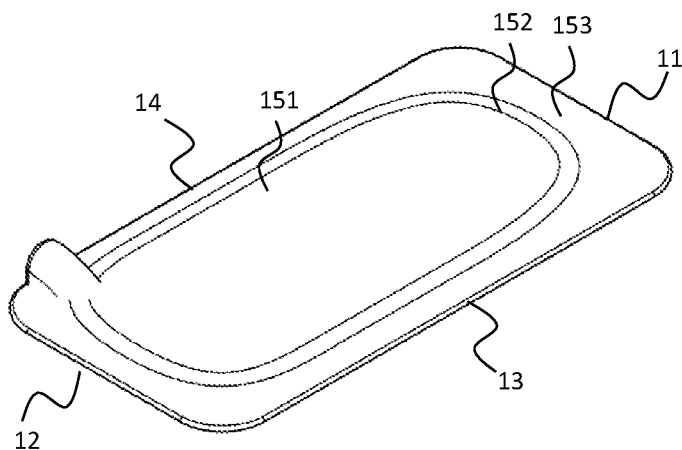

With reference to FIG. 3a, the degree of curvature of the first surface 15 increases in the longitudinal direction from a central region 151 of the first surface 15 of the substrate 10 towards the distal end 11 of the substrate 10. The curvature of the first surface 15 also increases in the longitudinal direction from the central region 151 towards the proximal end 12 of the substrate 10. Similarly, with reference to FIG. 3b, the degree of curvature of the first surface 15 increases in the transverse direction from the central region 151 of the first surface 15 of the substrate 10 towards the first side 13 the substrate 10. The curvature the first surface 15 also increases in the longitudinal direction from the central region 151 towards the second side 14 of the substrate 10. The curvature of the first substrate 15 of the substrate 10 is such that the substrate 10 tapers in thickness from a central region of the substrate 10 towards the ends and sides of the substrate 10.

The degree of curvature of the first surface 15 changes in steps in this embodiment, although a continuous change may be provided in alternative embodiments. By increasing in steps, the first surface 15 has discrete regions, each region having a constant radius of curvature, but with the radius of curvature changing from one region to the next. In particular, at least three curved regions are provided in the present embodiment, the central region 151, a first outer region 152 and a second outer region 153, wherein the first outer region 151 is located between the central region 151 and the second outer region 152. The central region 151 has a first radius of curvature R1, the first outer region 152 has a second radius of curvature R2 and the second outer region 153 has a third radius of curvature R3, where R1>R2>R3.

The curvature of any one or more of the curved regions 151, 152, 153 can be part-spherical. In this embodiment, the curvature at the central region 151 is part-spherical and substantially follows the spherical curvature of the eye. The first surface 15 is configured to lie against the inside of the scleral. The relatively low, part-spherical curvature of at least the central region 151 of the first surface 15 reduces the amount of static pressure exerted against the sclera when the implantable device 1 is in the implantation position between the sclera and choroid. Nevertheless, the relatively high curvature of the outer regions 152, 153 of the first surface can assist in the insertion of the substrate 10 between the tissue layers of the eye. The substrate 10 can be pushed into place between the tissue layers, causing separation of the tissue layers. The relatively high curvature can assist in separating the tissue layers, essentially opening up a pocket in which the implantable device locates. The curvature of the substrate 10 may ease surgical placement and forces. Moreover, the curvature may help support the incision 50 in the eye 5 through which the implantable device 1 is implanted in the eye 5.

Figure 4A:
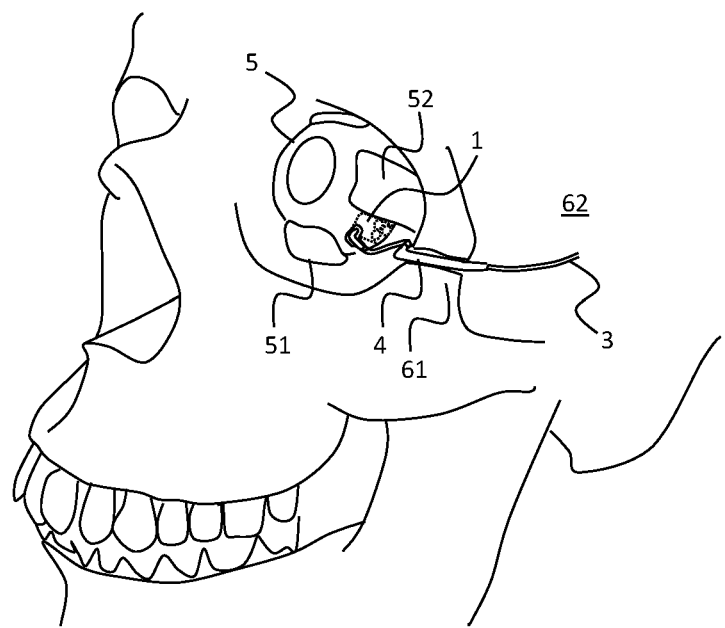
FIGS. 4a and 4b show perspective and side views, respectively, of the apparatus of FIG. 1 located relative to a skull.
Figure 4B:
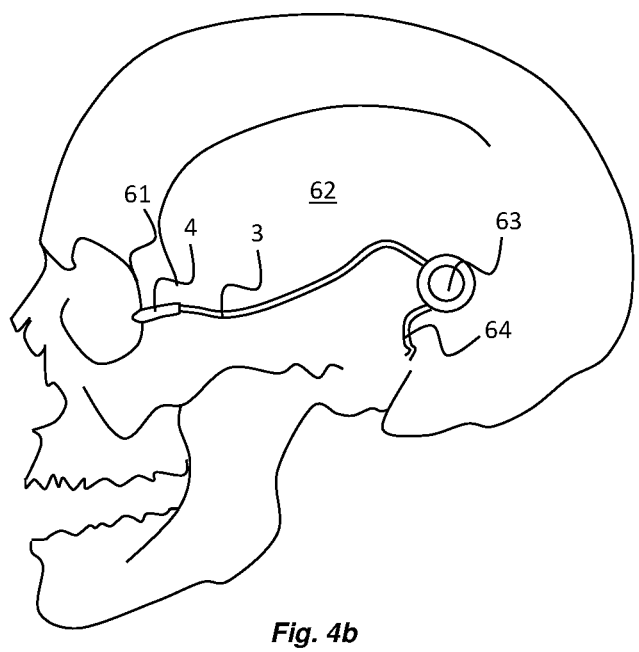

With reference to FIGS. 4a and 4b, the lead 3 is arranged to extend from the implantable device 1, through the incision in the sclera 51 of the eye 5, from the eye 5 to the adjacent orbital bone 61, around the orbital bone 61 and along the side of the patient's skull 62 to an electronics unit 63, which electronics unit 63 may comprise one or more of: an electrical stimulator for delivering electrical signals to the electrodes, an electrical amplifier for amplifier electrical signals received from the electrodes and a communications interface, for example. Components of the electronics unit 63 may be provided in a housing or 'can'. The housing may be a biocompatible metal housing, such as a titanium can. A return electrode 64 is connected to the electronics unit 63. The communications interface can allow for connection between the implantable device and an external electrical component such as a signal generator, signal processing device, a controller or otherwise.

Figure 5:
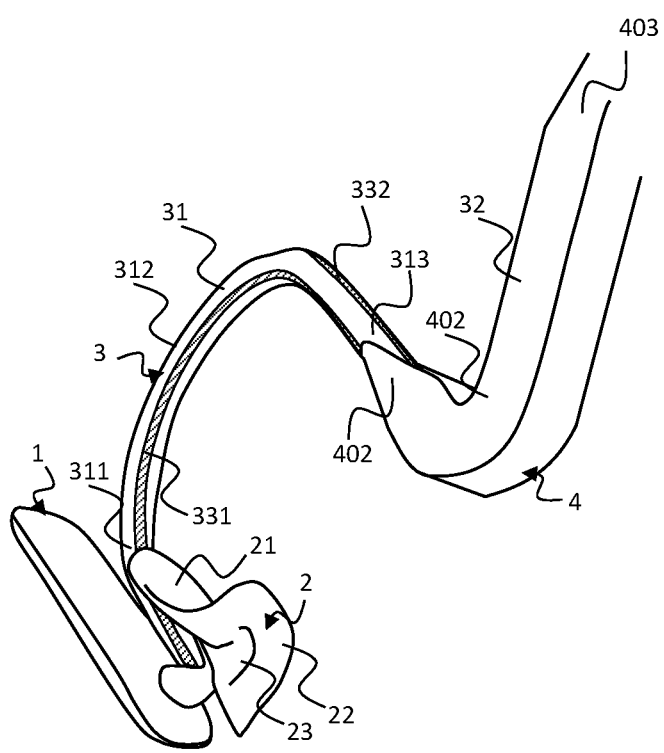
FIG. 5 shows an oblique view of the apparatus of FIG. 1, with an anchor device in a partially pre-folded configuration.

Referring also to FIG. 5, the lead 3 includes first and second lead sections 31, 32 that locate externally to the eye when the implantable device 1 is implanted in position. The second lead section 32 is configured to extend around the orbital bone 61 and the first lead section 31 is configured to locate between the implantable device 1 and the second lead section 32. The first lead section 31 has a pre-formed bend and specifically a pre-formed U-shaped bend, in this embodiment. The pre-formed bend provides a change in direction of the lead at the first lead section of about 180 degrees, although other angles may be utilised. The pre-formed bend has a radius of about 1.5 mm to 3 mm, although other radii may be utilised. Moreover, more than one pre-formed bend may be provided at the first lead section 31.

The pre-formed bend of the first lead section 31 bends in a posterior direction when the implantable device is implanted in the eye, as shown in FIG. 4a. Thus, ends 311, 313 of the U-shaped bend locate anteriorly of a middle-section 312 of the U-shape.

The first lead section 31 is flexible and has a length that is greater than the distance between the eye 5 and the orbital bone 61 and, more specifically, a length that is greater than the distance between the incision 50 of the eye 5 at which the lead 3 exits the eye, when the eye is in a forward-facing position, and a point on the orbital bone 61 to which the lead 3 makes contact as it extends around the orbital bone 61.

During use of the electrical apparatus, the eye 5 can rotate. To allow relatively unhindered rotation of the eye 5 when the implantable device 1 is implanted in the eye 5, the lead flexes and moves. Without the flexing and moving of the lead 3, the lead 3 would hinder or prevent movement of the eye 5 in one or more rotational directions. Essentially it might fix the position of the eye 5 relative to the orbital bone 61. By providing a first lead section 31 that is flexible and that has a length that is greater than the distance between the eye 5 and the orbital bone 61, the eye can move substantially in all rotational directions. As the eye rotates, depending on the direction of rotation, regions of the first lead section 31 collect together (concertina) or extend apart (straighten). By providing the first lead section 31 with the pre-formed bend, the amount of force required to cause the first lead section 31 to concertina or straighten is significantly lower, reducing discomfort to the patient and/or potential eye damage.

The pre-formed bend of the first lead section 31 in the present embodiment is formed subsequent to moulding of the first lead section 31. The first lead section 31 comprises the conductors 33 embedded in a surrounding cladding layer. The cladding layer is formed of silicone or other polymeric material, such as polyurethane, that is cured during the moulding process. The pre-formed bend is formed using a post-curing technique and specifically by rolling or holding the first lead section about a curved or angled surface while subjecting the first lead section to heating for a period of time. The curved or angled surface is at least part-cylindrical surface and has a radius of curvature of about 1.5 mm to 3 mm in this embodiment. The heating is conducted at a temperature of about 135° C. for a period of time of about 120 minutes, although other curvatures, temperatures and timings can be employed.

In the present embodiment, the second lead section 32 includes a reinforcement device 4 that provides for a thickening of the second lead section. The reinforcement device 4 directs the lead around the orbital bone 61 of the eye socket, as shown in FIGS. 4*a* and 4*b*, and provides protection for the lead and its conductors 61 against high stresses at this region. The reinforcement device 4 has a bend region 402, a first section 401 on the implantable device side of the bend region 402, and a second section 403 on the communications interface side of the bend region 402.

The reinforcement device 4 is arranged to be attached to the orbital bone 61. For example, the reinforcement device can be located in a notch formed in the orbital bone 61 to assist with attachment to the orbital bone 61. The notch can include a recessed groove to receive the reinforcement device 4 and an access opening through which the reinforcement device 4 is locatable in the recessed groove. The access opening may be narrower than the recessed groove. The reinforcement device may be squeezed through the access opening into the recessed groove where it remains substantially trapped in position at the orbital bone. The point at which the lead extends around the orbital bone 61, at which the notch is located, is lower than a transverse plane extending through the centre of the eye. In a posterior direction, the groove of the notch is angled inferiorly, by about 15 degrees.

The reinforcement device 4 is formed integrally with the second lead section 32 in this embodiment, e.g. by a moulding technique or otherwise, but may be a discrete component in alternative embodiment. For example, in alternative embodiments, the reinforcement device may be clipped to and/or glued in position at the second lead section 32.

The second lead section 32 and the reinforcement device 4 at the second lead section 32 has at least one pre-formed bend configured to conform to the angle of the orbital bone 61 such as to navigate the second lead section 32 around the orbital bone 61. The pre-formed bend at the second lead section 32 is formed through a post-curing technique, e.g., in the same manner that the pre-formed bend of the first lead section 31 is formed.

The pre-formed bend of the second lead section 32 has a sharper angle than the pre-formed bend of the first lead section 31. In particular, the pre-formed bend of the second lead section 32 is a V-shaped bend. In combination, the bends at the first and second lead sections 31, 32 provide the lead 3 with an S-shaped configuration or more specifically a 2-shaped configuration (i.e. a configuration shaped substantially like the number 2). The bends at the first and second lead sections bend in opposite directions. The bend at the first lead section 31 bends in a posterior direction as described above and the bend at the second lead section 32 bends in an anterior direction.

With reference to FIG. 5, the lead 3 has one or more stripes 331, 332 extending along the lead 3. The one or more stripes 331, 332 assist with placement of the lead 3 during implantation of the implantable device 1. Specifically, the stripes 331 provide a visual indication to the surgeon implanting the device regarding whether or not the lead 3 is twisted. The one or more strips 331, 332 extend along at least the first lead section as shown in FIG. 5, although they may extend along the entire length of the lead 3. The stripes 331, 332 can be formed from a layer of titanium dioxide or other material that has a contrasting colour to adjacent parts of the lead. Two of the stripes 331, 332 can be provided, each stripe 331, 332 being located at substantially opposite sides of the lead 3.

As indicated above, the electrical apparatus includes an anchor device 2. The anchor device 2 is provided to anchor the lead 3 at the outer surface of the eye 5, at or adjacent the incision 50 in the eye 5 through which the lead 3 extends, and to route the lead 3 away from the eye. The anchor device 2 is flexible and formed of polymeric material such a medical grade silicone or polyurethane with a stiffening element embedded at one or more portions therein, such as a mesh, e.g. polyethylene terephthalate mesh (Dacron™ mesh). The anchor device 2 is in the form of a patch or flap with a preformed shape, e.g. channel 23, that is adapted to receive a portion of the lead 3 when it secures the lead 3 to the outer surface of the eye 5.

Figure 6A:
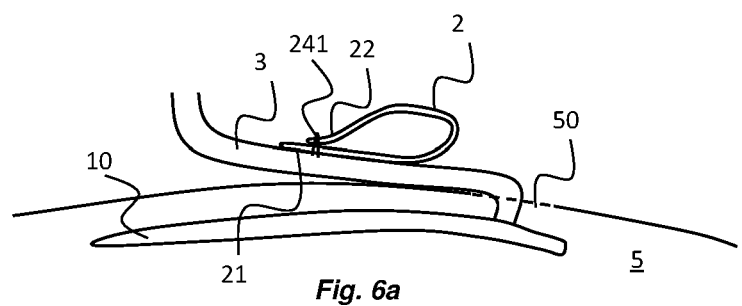
FIGS. 6a and 6b show the anchor device of FIG. 1 in a folded configuration and FIG. 6c shows the anchor device of FIG. 1 in an extended configuration.
Figure 6B:
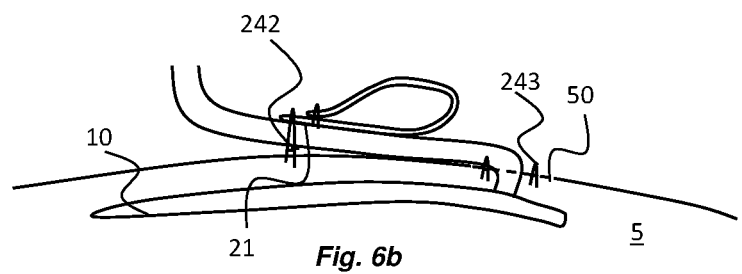
Figure 6C:
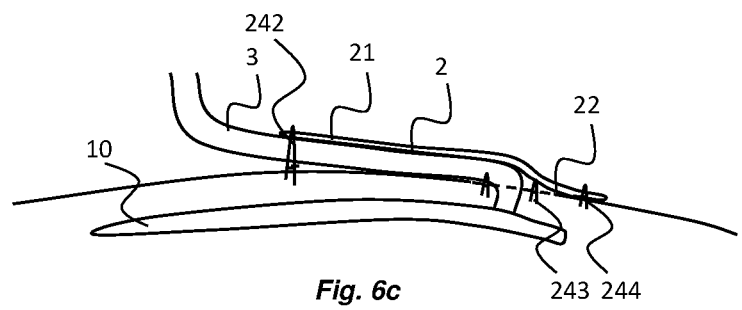

The anchor device 2 includes a proximal end portion 21 fixed to the lead 3 and a distal end portion 22 connected to the proximal end portion. Prior to implantation of the implantable device 1, e.g. during the manufacturing process, the anchor device 2 is releasably secured in a folded configuration in which the distal end portion 22 projects towards the proximal end portion 21, as illustrated in FIG. 6*a*. The releasable securing of the anchor device 2 in the folded configuration is achieved by providing at least one suture 241 to suture the distal end portion 22 to the proximal end portion 21, although other releasable fixation means may be employed such as adhesive.

While the anchor device 2 is in the folded configuration, the proximal end portion 21 may be secured to the outer surface of the eye 5, e.g., using one or more sutures 242.

By releasably securing the anchor device 2 in the folded configuration, the distal end portion 22 of the anchor device 2 can be temporarily held away from the incision 50 in the outer surface of the eye 5 through which the lead 3 exits the eye. Accordingly, the distal end portion 22 does not block or obstruct access to the incision 50 in the outer surface of the eye 5. By maintaining such access to the incision 50, sutures 243 can be applied more easily at the incision 50 in the outer surface of the eye 5, e.g. to close up the incision 50 (see FIG. 6*b*), and/or other treatment can be more easily applied at or adjacent the incision. Once such steps have been completed, the suture 241 securing the distal end portion 22 to the proximal end portion 21 can be released, whereupon the distal end portion 22 automatically, or through manipulation, projects away from the proximal end portion 21 (see FIG. 6*c*). The distal end portion 22 can then at least partly cover the incision 50 in the outer surface of the eye 5. In general, the anchor device 2 can extend over the lead 3 and cover at least part or all of the incision 50 in the outer surface of the eye 5.

The proximal and/or distal end portions 21, 22 of the anchor device 2 can be secured to the outer surface of the eye 5 using one or more sutures 242, 244 or other fixation means. In some embodiments, alternatively or additionally, one or more side portions of the anchor device 2 may be securable to the outer surface of the eye 5 using one or more sutures or other fixation means.

With reference to FIGS. 29*a*, 29*b*, 30*a* and 30*b*, any anchor device 2', 2" according to the present disclosure, whether it is folded or otherwise, may include one or more recesses 25', 25", each configured to receive a respective suture knot 246', 246" of sutures 242', 242" used to secure the device to the surface of an eye 5. The recesses 25', 25" may be discrete recesses as shown in the Figures, or otherwise connected together. In the embodiment of FIGS. 29*a* and 29*b*, for example, the recesses 25' are each provided as depressed portions on the top surface of the anchor device 2', e.g. at side portions of the anchor device 2'. In an alternative embodiment, shown in FIGS. 30a and 30b, the recesses 25" are provided on the underside of the anchor device 2", e.g. at side portions of the anchor device 2", to create pockets between the anchor device 2" and the outer surface of the eye 5. In use, once each suture 242', 242" has been tied off, the suture may be rotated to position the suture knot 246', 246" in the respective recess 25', 25". In the embodiment of FIGS. 29a and 29b, the suture knot 246' may be pulled through the material of the anchor device to access the pocket.

In general, when secured to the outer surface of the eye 5, the anchor device 2, 2', 22" provide supports and stabilisation for the lead as it extends out of the incision 50 in the outer surface of the eye 5. Furthermore, the anchor device shields the incision 50 in the outer surface of the eye 5. The anchor device 2 also serves to route the lead 3 in an appropriate direction away from the anchor device 2 and the eye 5, e.g., past extraocular muscles of the eye and towards the lateral orbital rim 61. To achieve this routing, the lead 3 at the anchor device follows a bent path.

As discussed above, the implantable device 1 according to the present disclosure includes a substrate 10 and electrodes 17 partially embedded in the substrate 10. The substrate 10 is formed primarily of a first, non-conductive material; and the electrodes are formed of a second, conductive material. As will now be described with reference to FIGS. 7a to 7d, each electrode 17 includes apertures 171 through which the first material of the substrate 10 at least partially extends to anchor the electrode 17 to the substrate 10.

Each electrode 17 is substantially flat and with a first surface 172 and an opposite second surface. Each electrode 17 has a circular disk shape. The first surface 172 of the electrode faces away from the substrate 10 and is partially exposed from the substrate 10 to enable electrical contact with tissue of the eye 5. The second surface of the electrode 17 is buried within the substrate 10 and specifically the first, non-conductive material of the substrate 10. Each aperture 171 of the electrode 17 has open ends at the first and second surfaces of the electrode 17.

In this embodiment, a plurality of the apertures 171 are provided in each electrode 17, adjacent a peripheral edge of the electrode 17. The apertures 171 are uniformly spaced and positioned in a ring pattern adjacent the peripheral edge of the electrode 17 and positioned within the outer 10 or 15% of the diameter of the electrode 17. Each aperture 171 has a diameter that is less than 15% of the diameter of the electrode 17. For example, each aperture may have a diameter of between 100 µm and 800 µm. Each aperture may be circular, although other aperture shapes can be used.

The first, non-conductive material is a flowable polymeric material such as a silicone elastomer or polyurethane that is set during the manufacturing process to form the substrate 10. While in the flowable state, and prior to setting, the first material can flow into each aperture 171 to fill the aperture, generally as represented by arrows 102 in FIG. 7d. The first material can extend out of the aperture 171 via the open ends of the aperture 171, whereupon the first material can extend transversely to the aperture 171 across surfaces of the electrode 17. The first material can form a continuous loop that extends through each aperture 171 and around a periphery of the electrode 17 and through other apertures 171. Thus, each electrode 17 is trapped between portions of the first material, assisting in the anchoring of the electrode 17 to the substrate 10.

Figure 7A:
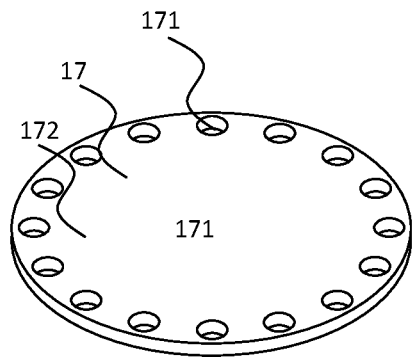
FIG. 7a shows an oblique view of an electrode of the implantable device of FIG. 1.
Figure 7B:
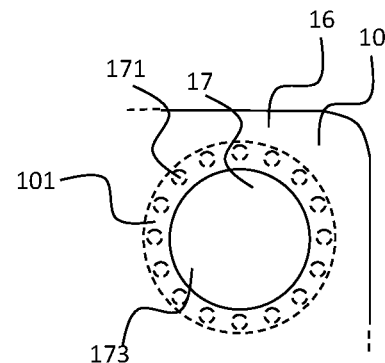
FIG. 7b shows the electrode of FIG. 7a embedded in a substrate of the implantable device of FIG. 1.
Figure 7C:
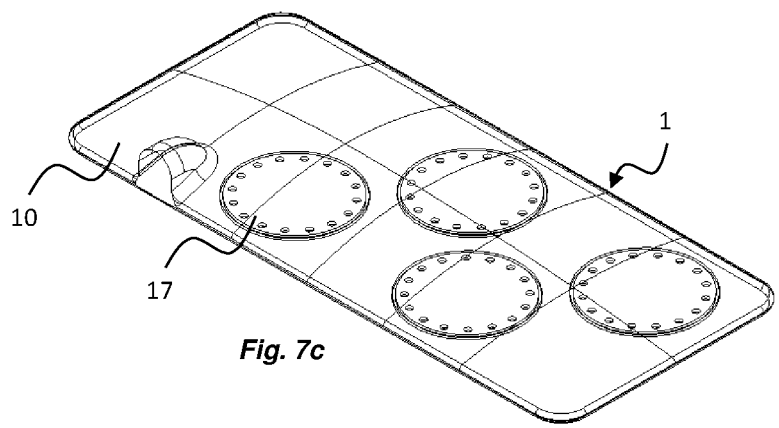
FIG. 7c shows an oblique view of the substrate with a plurality of the electrodes embedded therein.
Figure 7D:
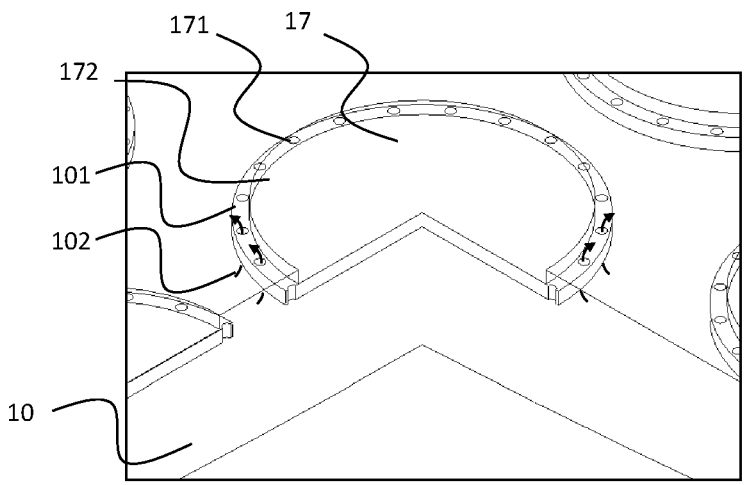
FIG. 7d shows a cross-sectional oblique view of electrodes of FIG. 7c embedded in the substrate.

As shown in FIGS. 7b and 7d, the substrate 10 provides a lip 101 of the first material that extends around the periphery of the first surface 172 of each of the electrodes 17 to assist with anchoring the electrodes 17 to the substrate, while leaving a central region 173 of the first surface 172 of each electrode 17 exposed. In this embodiment, the first material extends through the apertures 171 underneath the lip 101. Thus, the apertures 171 enhance the function of the lip 101 as a means of assisting anchoring of the electrode 17 to the substrate 10.

Figure 8C:
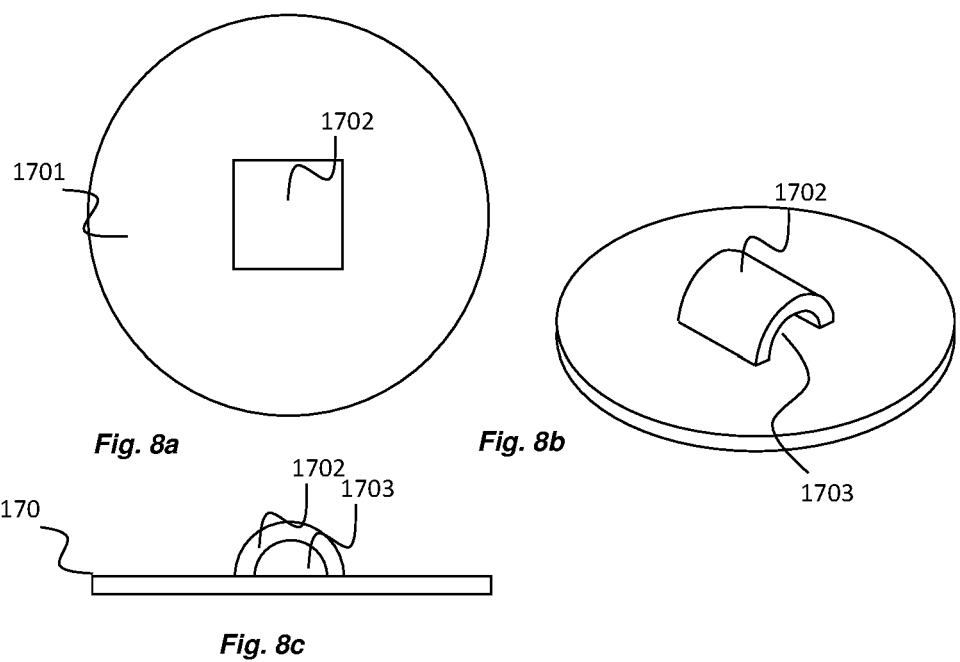
Figure 9C:
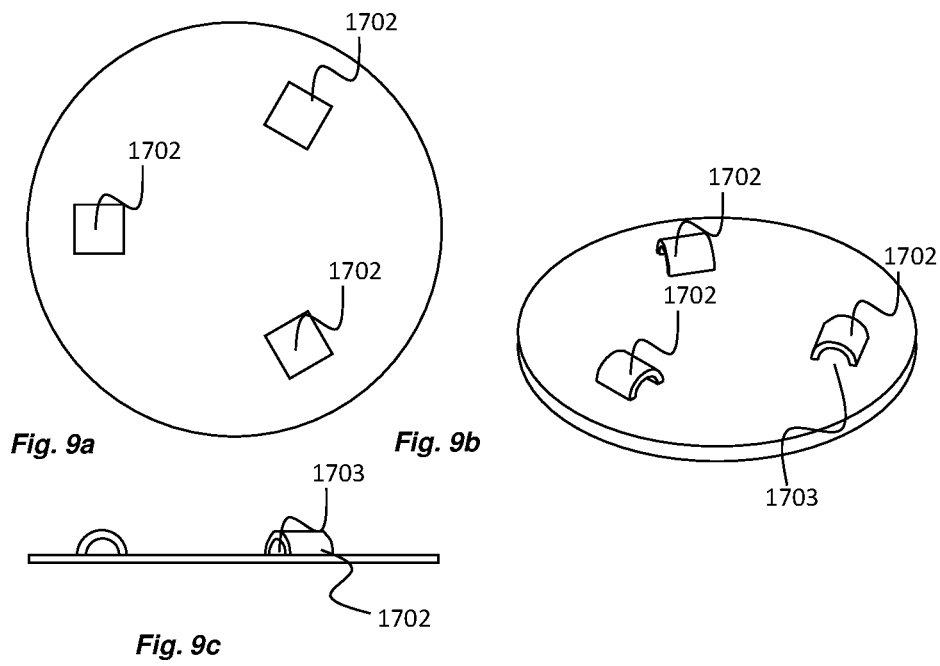
Figure 10A:
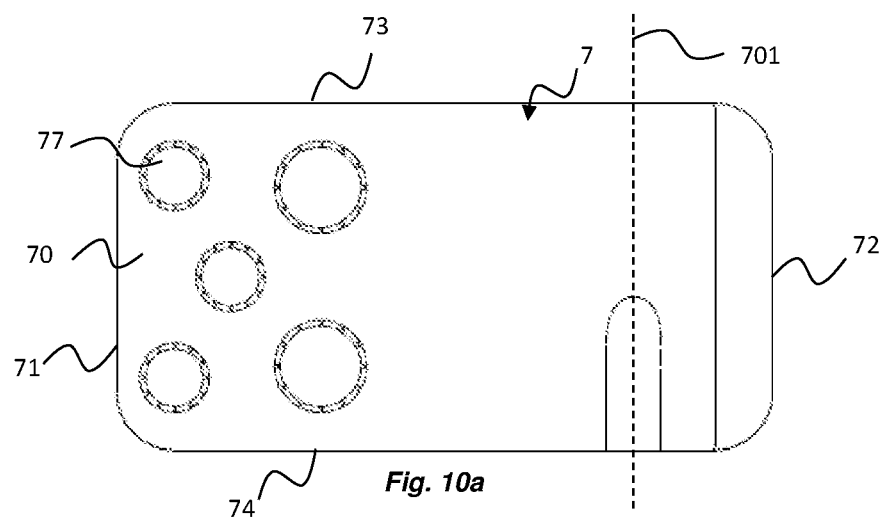
FIG. 10a shows a top view of an implantable device for implanting in an eye according to another embodiment of the present disclosure.
Figure 10B:
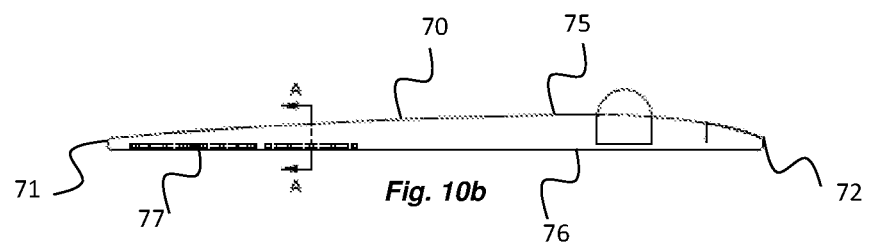
FIGS. 10b and 10c show side and end views, respectively, of the implantable device of FIG. 10a, and FIG. 10d shows a cross-section of the implantable device of FIG. 10a taken along line A-A of FIG. 10b.
Figure 10C:
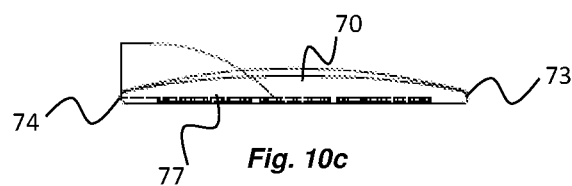
Figure 10D:
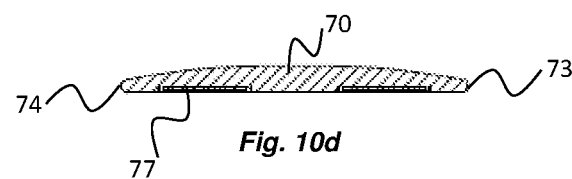

In addition to or as an alternative to providing apertures 171 that extend between the first and second opposite surfaces of the electrode 17, at least one aperture may be defined by a projection on the second surface of the electrode. For example, with reference to FIGS. 8a to 8c, the second surface 1701 of an electrode 1700 can include a projection such a loop, handle and/or hoop 1702, the centre of which provides the aperture 1703 through which first material of the substrate 10 extends. The second surface 1701 of the electrode 170 is buried within the substrate. By providing the projection 1702 at the second surface that defines the aperture 1703, the first material of the substrate can extend through the aperture 1703 when the second surface is buried within the substrate during manufacturing of the device, e.g., while the first material of the substrate is in a flowable state as discussed above. In some embodiments, as illustrated in FIGS. 9a to 9c, a plurality of the projections 1702 can be provided, each defining at least one aperture 1703.

The implantable devices of the present disclosure include a plurality of electrodes that can be used to electrically stimulate the eye. In some embodiments, electrical current may be applied to a plurality of the electrodes simultaneously. For example, two or more of the electrodes 17, shown in FIG. 1, for example, can be electrically grouped. Electrical current can be applied simultaneously to electrodes of the group. The electrodes of the group can be electrically addressed in parallel or can be ganged together. The simultaneous addressing of the electrodes 17 can provide an increased penetration of the electric field into tissue, leading to better efficacy. Moreover, reduced power consumption may be achieved as a result of lower impedances and lower charge required per electrode.

In an alternative embodiment, as shown in FIGS. 10a to 10d, an implantable device 7 is provided having a flexible substrate 70 with a distal end 71, a proximal end 72, a first side 73 and a second side 74. The substrate 70, when viewed from above, is substantially rectangular, with curved corners to minimise surgical trauma. The longitudinal direction (length) of the substrate extends between the distal and proximal ends 71, 72 and the transverse direction (width) of the substrate extends between the first and second sides 73, 74. The substrate 70 includes first and second opposite surfaces 75, 76 that each extend between the distal and proximal ends 71, 72 and between the first and second sides 73, 74.

Electrodes 77 are partially embedded in the substrate, which electrodes 77 are used to apply electrical current to tissue of the eye for the purposes of therapeutic stimulation and/or are used to monitor properties of the eye by receiving electrical current from tissue of the eye. In this embodiment, five electrodes 77 are provided although other numbers of electrodes may be used. The electrodes 77 are exposed at the second surface 76 of the substrate. The five electrodes 77 are clustered towards the distal end 71 of the substrate 70 such that, when implanted, the electrodes 77 are positioned substantially under the retina. In this embodiment, in the length direction of the substrate, the electrodes are all located in the distal half of the substrate, there being no electrodes located in the proximal half of the substrate.

The length of the substrate 70 is between about 10 mm and 12 mm, e.g. about 11.5 mm, although other lengths are possible. The width of the substrate 10 is between about 5 and 7 mm, e.g. about 6 mm, although other widths are possible. The electrodes 77 are disc-shaped electrodes with circular peripheries, although other shapes are possible. The diameters of the electrodes 77 are between about 0.5 mm and 2.5 mm, e.g., about 1 mm or 1.4 mm. The areas of the electrodes are correspondingly between about 0.2 $mm^2$ and 4.9 $mm^2$, e.g., about 0.8 $mm^2$ or 1.5 $mm^2$. However, as for the electrodes 17 described above, a lip surrounds the electrodes 77 such that only a portion of each electrode is exposed from the substrate.

In this embodiment, electrodes of different sizes are provided. A first group of electrodes have a smaller diameter (about 1 mm) than a second group of electrodes (about 1.4 mm). The first group of electrodes are located distally of the second group of electrodes. The electrodes of the first group may be used as active electrodes and the electrodes of the second group may be used as inactive (return) electrodes. Alternatively, however, all electrodes may be used as active electrodes, and one or more return electrodes may be located elsewhere, including as implanted electrodes or non-implanted electrodes (e.g. electrode needles contacted to skin on the back of the head or neck).

By providing multiple active electrodes and/or inactive electrodes a number of advantages may be achieved. For example, different combinations of active electrodes and/or inactive electrodes may be selected to enable the monitoring or application of electrical signals in different directions (different current vectors). Further, multiple electrodes may be ganged together to increase their effective area while having reduced impedances. Moreover, having additional electrodes allows for redundancy, e.g. in case of failure of one or more of the electrodes or associated electrical components.

In some embodiments, the implantable device may be configured such that at least the first group of electrodes is positioned beneath the retina and close to the central retina without infringing on the central retina. The distance between the first group of electrodes (or the distal-most electrode or electrodes of the first group of electrodes) and the proximal end of the substrate may be configured accordingly to facilitate this positioning. In one example, the length of the substrate 70 is 11.35 mm, the distal-most pair of the first group of electrodes is positioned about 10 mm (e.g. 9.95 mm in one example) from the distal end of the substrate. The point at which the lead separates from the substrate (indicated for example by dashed line 701 in FIG. 10*a*), is positioned about 2 mm from the proximal end 72 of the device. In this embodiment, the device is configured to be implanted such that the proximal end of the device is positioned about 3 mm from the limbus, thereby to position the distal-most pair of electrodes close to the central retina. The point at which the lead separates from the substrate may be substantially aligned with the incision point.

Figure 11A:
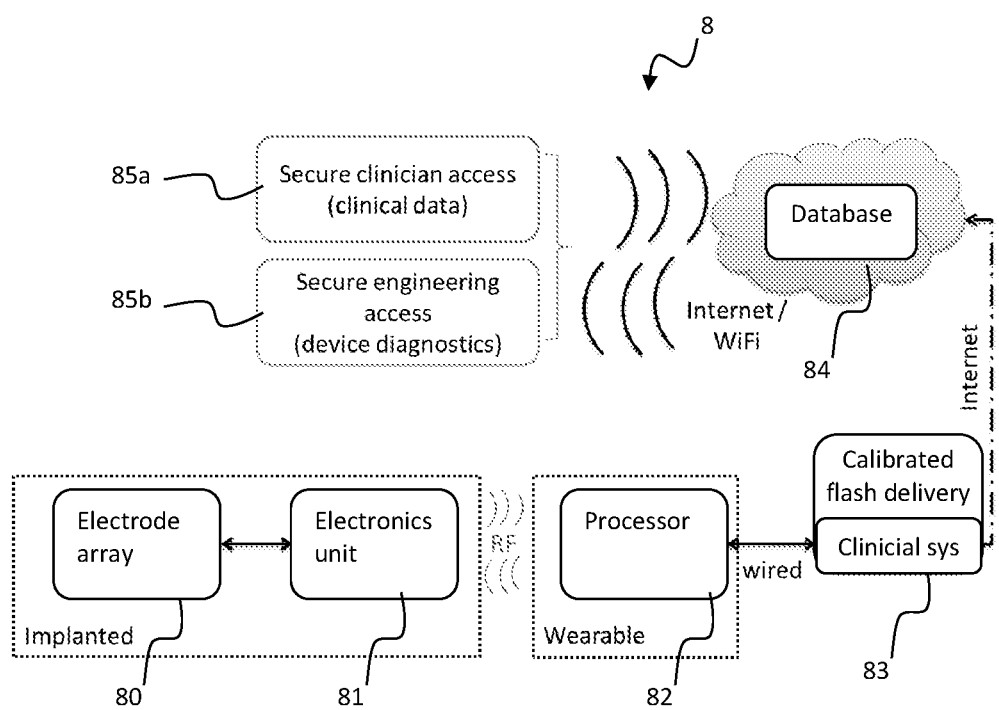
FIG. 11a shows a system diagram illustrating electrical apparatus according to an embodiment of the present disclosure.

With reference to FIG. 11*a*, in one embodiment of the present disclosure there is provided electroretinography (ERG) apparatus 8 for monitoring an eye of a patient and in particular to measure electrical responses of the retina of the eye to a stimulus such as electrical or light stimulation. The apparatus includes implanted components, including an implantable device 80 that is implanted between the sclera and choroid layers of the eye and includes one or more electrodes, and an electronics unit 81. The implantable device 80 and electronics unit 81 may be configured in accordance with, for example, the implantable devices 10, 70 and electronics unit 63 of any one of the preceding embodiments or otherwise.

The electronics unit 81 is configured to amplify low level electrical signals sensed by the one or more electrodes in response to the stimulus (electrical or light stimulation), before transfer of the signals to an external processing device 82 of the apparatus. The external processing device 82 may be worn by the patient, e.g., on the side of the patient's head, aligned with the electronics unit 81. In this regard, the device 82 may be a wearable device. Transfer of the electrical signals to the external processing device 82 may be via a wireless connection, e.g. an RF connection, inductive link, or otherwise, which transfers signals through tissue layers at the side of the patient's head or elsewhere, although alternatively a wired or direct connection may be provided. The electronics unit 81 may include an implanted inactive (return) electrode. In alternative embodiments, one or more electrodes of the implantable device 80 may be employed as inactive electrodes.

The processing device 82 may deliver the electrical signals, e.g., by first converting them from a digital to an analogue form, to an ERG system that may be connected via wire or wirelessly to the processing device 82. The ERG system may be a clinical ERG system 83 that may be a system that is known in the art, but which is typically intended to receive electrical signals from one or more electrodes located on a surface of the eye, rather than being implanted in the eye. Alternatively, the ERG system may be a system made for specific use with the implantable and wearable components 80, 81, 82 of the present disclosure. The ERG system 83 may be configured to control a stimulus to the implanted eye, e.g. an electrical or light stimulus. For example, the ERG system may include a controller to control a light, in order to provide for calibrated delivery of flashes in the field of view of the implanted eye. The controller may also control, e.g. trigger, the recording of ERG signals using the implanted components 80, 81 through communication with the processing device 82.

The system 83 may communicate with a database such as a cloud database 84, which may be include secure access for clinicians 85*a* and/or secure access for engineers 85*b*, to enable ERG results to be accessed remotely, e.g. for the purpose of tracking of disease progress or system performance. The ERG system 83 may include processing components and may generally be configured to present electroretinograms and/or associated data to a user such as a clinician. The ERG system 83 may include a display to display results of ERG testing.

In use, the patient may be seated and eye drops may be applied to the patient's implanted eye to dilate the eye. The patient may be dark-adapted, e.g. for 20 minutes, in a dark room. Before or after this process, the processing device 82 of the apparatus may be connected to the clinical ERG system 83. Optionally, an electrode is contacted with the patient, e.g. on the forehead skin, if an external inactive electrode is to be used in place of the implanted inactive electrodes described above. The clinical ERG system 83 is then used to control electroretinography testing by controlling delivery of light flashes and controlling the recording of ERG signals using the implanted components 80, 81 and processing device 82, and receive and present the results of testing. The clinical system may upload raw and processed data to the cloud database 84, e.g. via the internet. A server may be associated with the cloud database that performs further processing of the uploaded data. Clinicians and engineers may access the patient ERG data via the server.

Figure 11B:
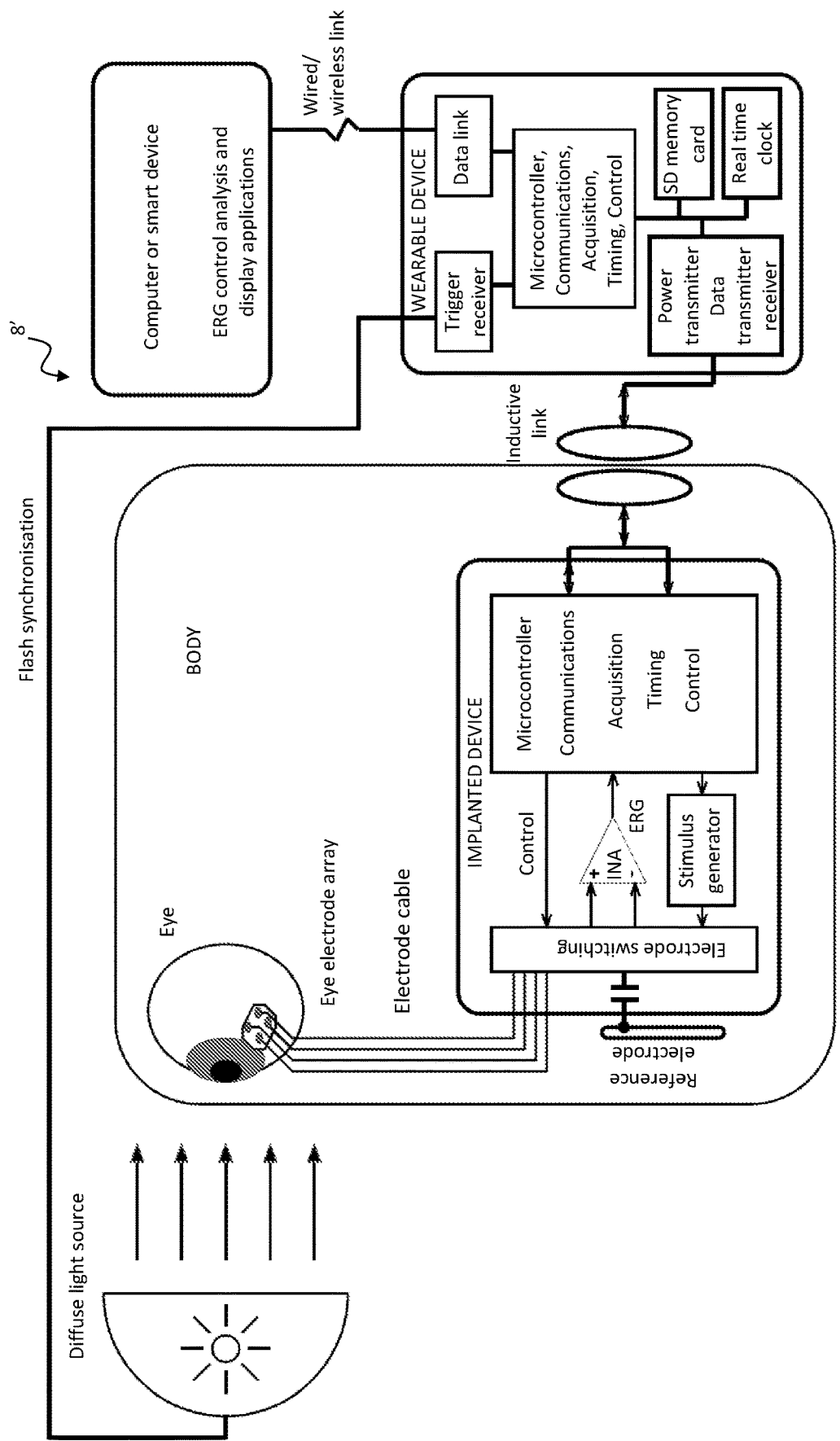
FIG. 11b shows a system diagram illustrating electrical apparatus according to another embodiment of the present disclosure.

With reference to FIG. 11b, an electroretinography apparatus 8' for monitoring an eye of a patient and in particular to measure electrical responses of the retina of the eye to stimulus (electrical or light stimulation) is provided, the apparatus being generally in accordance with the apparatus 8 described above with reference to FIG. 11a, and employing components designed specifically for use with the implantable electronic array and electronics unit according to the present disclosure.

Figure 12:
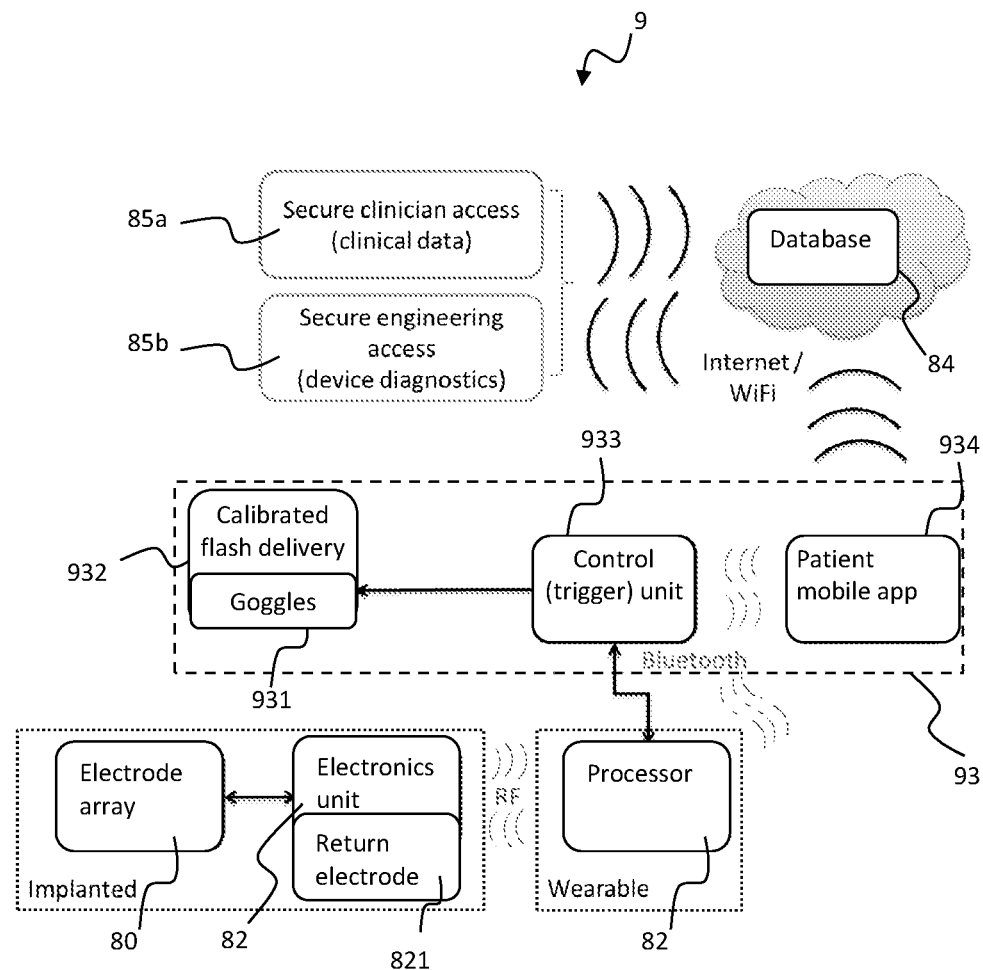
FIG. 12 shows a system diagram illustrating electrical apparatus according to another embodiment of the present disclosure.
Figure 13:
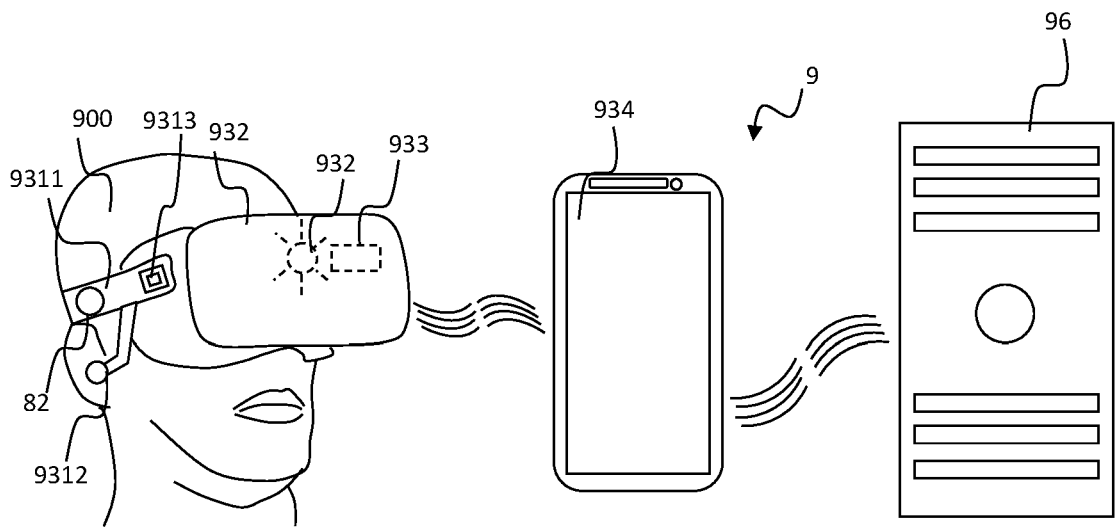
FIG. 13 provides an illustration of the electrical apparatus of FIG. 12 in use.

With reference to FIGS. 12 and 13, in another embodiment of the present disclosure there is provided electroretinography apparatus 9 that is similar to the electroretinography apparatus 8 of the embodiment of FIG. 11a, including the same or similar implanted device 80, electronics unit 81, processing device 82, database 84 and clinician and engineer database access points 85a, 85b, but in which the ERG system 83 (e.g. the clinical ERG system) is replaced with a mobile ERG system 93.

The mobile ERG system 93 includes eyewear 931 such as goggles. The eyewear 931 is adapted to be worn over the eyes of the patient 900 to cover the eyes (and part of the face) of the patient 900, as illustrated in FIG. 13, placing the eyes in complete or almost complete darkness. When worn, the eyewear 931 defines a dark inner chamber, located between inner walls of the eyewear and the patient's face and eyes. Accordingly, the eyewear 931 can enable a patient to be dark-adapted without necessarily requiring the patient to be located in a dark room.

In this embodiment, the processing device 82 is configured to locate at the side of the head of the patient 900 in order to align with the implanted electronics unit 81. The processing device 82 may, for example, be conveniently positioned on a headband 9311 of the eyewear 931 to achieve the alignment.

In this embodiment, the eyewear 931 include a light 932, e.g. an LED, and a controller 933 adapted to control flashing of the light 932. The light 932 is located in or adjacent to the internal chamber of the eyewear 931 so that flashes of the light are presented within the internal chamber and therefore within the field of view of the patient's implanted eye.

In this embodiment, the controller 933 is also adapted to control, e.g. trigger, the recording of ERG signals using implanted components 80, 81 and processing device 82. The controller 933 is also adapted to communicate, e.g. wirelessly, with a mobile computing device 934, e.g. an app-based computing device such as a Smartphone or tablet. In alternative embodiments, the controller 933 may be comprised at least partially in the mobile computing device 934. The mobile computing device 934 may generally be configured to present electroretinograms and/or associated data, to a user such as a clinician. The mobile computing device may include a display to display results of ERG testing.

In use, the patient may be seated and eye drops may be applied to the patient's implanted eye to dilate the eye. The patient may don the eyewear and be dark-adapted, using the eyewear, e.g. for 20 minutes. The eyewear may include a speaker or headphones 9312 that play music or other audio recordings to the patient while the patient is dark-adapted. Additionally or alternatively, the speaker or headphones 9312 may be used to provide instructions for use of the apparatus 9.

Once dark-adapted, the patient or clinician may start the ERG recording process, e.g. by pressing a button 9313 or interacting with another interface on the eyewear 931, or pressing a button or interacting with another an interface of the mobile computing device 934. The mobile ERG system 83 is then used to control electroretinography testing by controlling delivery of light flashes using the light 932 and controlling the recording of ERG signals using the implanted components 80, 81 and processing device 82. The results of testing are provided, e.g. wirelessly, to the mobile computing device 934, which can present electroretinograms and/or associated data to a user. The mobile computing device 934 may upload raw and processed data to the cloud database 84, e.g. via the internet. A server 96 may be associated with the cloud database that performs further processing of the uploaded data. Clinicians or engineer may access the patient ERG data via the server 96.

ERG systems according to embodiments of the present disclosure, such as the mobile ERG system, may be particularly suited, for example, to home use or in clinics that do not have access to conventional, typically larger, ERG systems. This is made possible in part by use of electrodes that are pre-implanted in the eye, and do not need to be applied to the eye at the time of ERG testing. Therefore, lower-skilled clinicians may be employed to carry out the testing. Moreover, because the electrodes are implanted, the eyewear may be applied around the eyes of the patient without risk of disturbing the electrodes.

With reference to the sixth example study below, ERG methods or apparatus according to embodiments of the present disclosure (e.g. as discussed above with reference to FIGS. 8 to 13) may take advantage of an occurrence identified herein, that the polarity of ERG response signals, e.g. the polarity of ERG waveforms, that are recorded using the one or more implanted electrodes, can change depending on the location of the electrodes.

For example, apparatus 8, 8' or 9' having an implantable device with one or more electrodes as described above or otherwise may be used to: deliver stimulus to the patient's eye; measure an ERG response signal received at the one or more implanted electrodes resulting from the stimulus; and determine the location, or a change in location, of the one or more electrodes based on the polarity of the ERG response signal. For example, in some embodiments, a location of the electrode may be determined by: positioning the one or more electrodes at different locations in the eye; at each of the different locations, delivering stimulus to the patient's eye and measuring an ERG response signal received at the one or more electrodes resulting from the stimulus; identifying the polarities of the ERG response signals received at the different locations; identifying a difference between the polarities of the ERG response signals identified at two of the different locations; and determining a location of the one or more electrodes based on the difference in polarity occurring between the two of the different locations.

As evident from the sixth example study, the location where the polarity changes may be determined as a location beneath the retina of the patient's eye. In this regard, electrode locations to a side of the retina (e.g., beneath or anterior of the pars plana of the eye) may give rise to an ERG response signal having a first polarity, but when moved to an electrode location beneath the retina this may give rise to an opposite polarity of the ERG response signal.

In some embodiments, a change in location of the electrode may be determined by: delivering a first stimulus to the patient's eye; measuring a first ERG response signal received at the one or more electrodes resulting from the first stimulus; optionally delivering a second stimulus to the patient's eye; measuring a second ERG response signal received at the one or more electrodes resulting from the first stimulus (or second stimulus if used); comparing the polarities of the first and second ERG response signals; and determining a change in location of the one or more electrodes if the identified polarity of the first ERG response signal is different from the identified polarity of the second ERG response signal.

In some embodiments, the change in the location of the one or more electrodes may be identified as a change from the one or more electrodes being located beneath the retina of the patient's eye to the one or more electrodes being located to a side of the retina (e.g., beneath or anterior of the pars plana of the eye), or vice-versa.

In some embodiments, the determining of the location or change in location of the electrodes may be used to determine the location or change in location of the implantable device that comprises the electrodes.

In some embodiments, the apparatus or method may provide an indication of the determined location or change in location, of the one or more electrodes (and/or of an implantable device that includes the one or more electrodes), to a user, e.g. through display of corresponding information on a display screen.

In all embodiments described herein, because electrodes are implanted, anaesthesia may not be required during use. Still further, increased amplitude ERG recordings may be obtained due to the suprachoroidal positioning closer to the retina. Moreover, the suprachoroidal position may be particularly stable and biocompatible, without being prone to causing sub conjunctival erosion, for example.

Any controller or processing device used in the present disclosure may comprise one or more processors and data storage devices (computer readable media). The one or more processors may each comprise one or more processing modules and the one or more storage devices may each comprise one or more storage elements. The modules and storage elements may be at one site, e.g. in a single clinical ERG system, a single mobile computing device, etc., or distributed across multiple sites and interconnected by a communications network such as the internet.

The processing modules can be implemented by a computer program or program code comprising program instructions. The computer program instructions can include source code, object code, machine code or any other stored data that is operable to cause a processor to perform the methods described. The computer program can be written in any form of programming language, including compiled or interpreted languages and can be deployed in any form, including as a stand-alone program or as a module, component, subroutine or other unit suitable for use in a computing environment. The data storage devices may include suitable computer readable media such as volatile (e.g. RAM) and/or non-volatile (e.g. ROM, disk) memory or otherwise.

Example 1

Suprachoroidal therapeutic stimulation was tested using a genetically modified rat model of retinal degeneration (P23H-3 retinal degeneration rats), which very closely mimics the human condition. The rats were divided into 3 groups of control (n=6), passive (n=6) and active stimulation (n=7). Animals in the passive and active stimulation groups had a platinum electrode implanted in one eye of each animal at 7 weeks of age. Animals in the passive group did not receive the stimulation. Animals in the active stimulation group received 1 hour of chronic micro-electrical stimulation (100 μA, 1 Hz (pulse per second)) twice per week for 4 weeks (equating to roughly 5 human years). Full-field electroretinography (ERG) was performed at 6-(baseline) and 12-(post-treatment) weeks of age as a surrogate measure of photoreceptor survival. The ERG responses of the 3 study groups were compared to determine the effect of electrical stimulation on photoreceptor survival.

Figure 14:
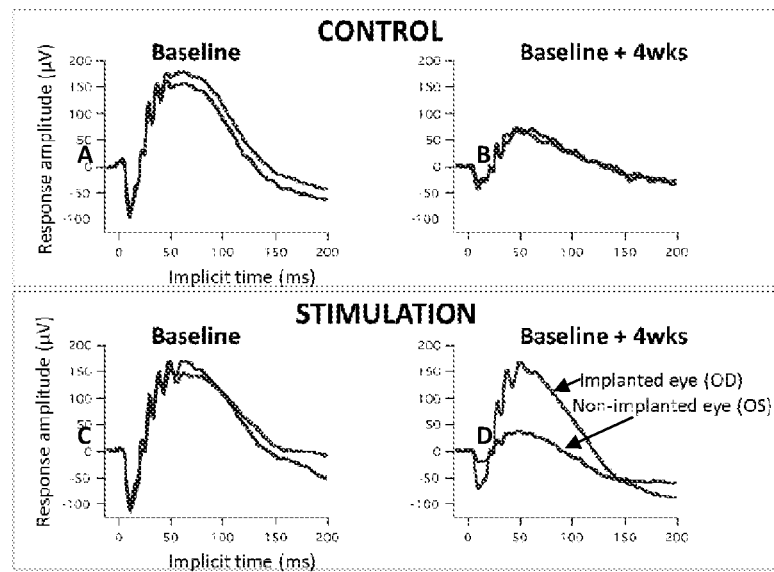
FIG. 14 shows, for a first example study, graphs (electroretinograms) of photoreceptor activity, from a rat with a genetic retinal degenerative condition that mimics the most common form of heredity blindness in people, wherein each graph illustrates activity for an eye including an implanted electrode device (OD) and for a fellow non-implanted eye (OS), and wherein (i) graph A shows initial activity at 0 weeks, and graph B shows activity at 4 weeks, when no stimulation is applied via the implanted electrode device and (ii) graph C shows initial activity at 0 weeks, and graph D shows activity at 4 weeks, when stimulation is applied via the implanted electrode device.
Figure 15:
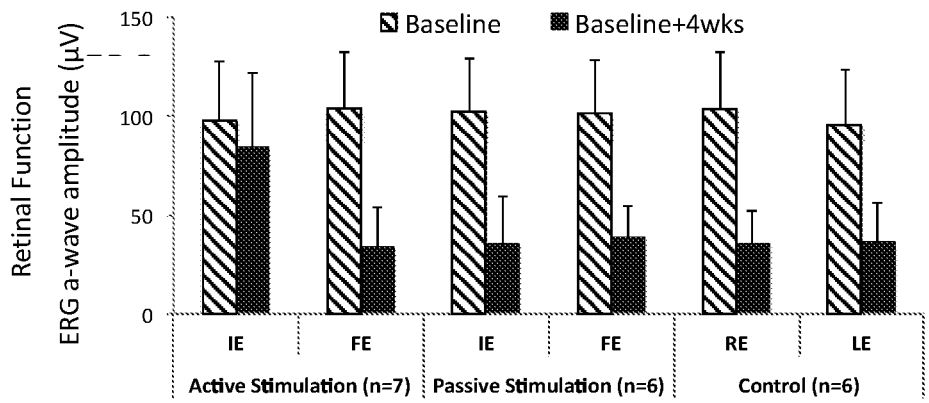
FIG. 15 shows, for the first example study, a bar graph of retinal function, recorded as an ERG a-wave amplitude ($\mu V$), from rats with a genetic retinal degenerative condition that mimics the most common form of heredity blindness in people, wherein each bar illustrates function for an eye including an actively stimulated implanted electrode device (IE) and its fellow non-implanted eye (FE), or for an eye including a passively (non-)stimulated implanted (sham) electrode device (IE) and its fellow non-implanted eye (FE), or for an eye including no implanted electrode device where the right or left eye provide controls (RE/LE), either at 0 weeks (baseline) when no stimulation is applied via the implanted electrode device or at 4 weeks of subsequent stimulation (baseline+4 wks)

With reference to FIGS. 14 and 15, the control (non-stimulated) eyes lost significant retinal function. However, retinal function was preserved in the active (stimulated) eyes. Retinal function was also lost in passive (sham) treated eyes.

Figure 16:
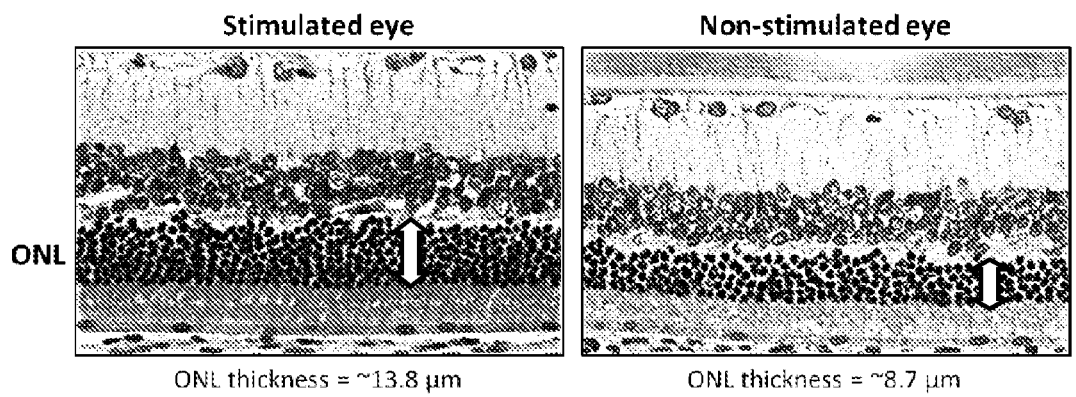
FIG. 16 shows, for the first example study, photomicrographs of tissue layers, including the outer nuclear layer (ONL) of the stimulated eye and the non-stimulated eye.

With reference to FIG. 16, histological analysis of outer nuclear layer (ONL) thickness revealed that photoreceptors were preserved in the stimulated eyes, the ONL containing cell bodies of the photoreceptors. The ONL was thicker in the stimulated eye compared to the non-stimulated eye, suggesting that suprachoroidal electrical stimulation preserves photoreceptor survival.

In the active stimulation group, it was further found that the ERG a-wave response amplitude at 12 weeks of age was slightly reduced in the stimulated eyes (83.8±38.1, p=0.413) but markedly reduced in the non-stimulated fellow eyes (33.7±19.7, p<0.001), compared to the baseline value at 6 weeks of age (100.3±29.9). The ERG a-wave amplitude of both eyes in the control and passive groups were markedly reduced at 12 weeks of age compared to the baseline value (p<0.001). Furthermore, the magnitude of ERG a-wave amplitude reduction in the control and passive groups was similar to that of the non-stimulated fellow eyes of the active stimulation.

Overall, chronic low-level electrical stimulation using a fully implanted electrode in the P23H-3 rat model of retinal degeneration preserved photoreceptor function, including when micro-electrical stimulation was applied suprachoroidally at a 'dosage' of about twice per week for 4 weeks.

Example 2

Suprachoroidal therapeutic stimulation was tested using a genetically modified rat model of retinal degeneration (P23H-3 retinal degeneration rats), which very closely mimics the human condition. The rats were divided into 3 groups of control (n=8), passive (n=8) and active stimulation (n=9). Animals in the passive and active stimulation groups had a platinum electrode implanted in the right eye of each animal at 7 weeks of age. Animals in the passive group did not receive the stimulation. Animals in the active stimulation group received 1 hour of chronic micro-electrical stimulation (95 μA, 1 Hz (pulse per second), five times per week for 8 weeks. Full-field electroretinography (ERG) was performed at 8, 10, 12, 14 and 16 weeks of age as a surrogate measure of photoreceptor survival. The ERG responses of the 3 study groups were compared to determine the effect of electrical stimulation on photoreceptor survival.

ERG data from the control animals showed, as expected, a gradual decline in photoreceptor function (decreased ERG a-wave amplitude) over the course of the study (FIG. 17). On average, there was approximately 40% reduction in ERG response after a period of 8 weeks.

The ERG a-wave amplitudes of the eye at various time points for the 3 study groups are shown in FIG. 18a. In the control group, the ERG a-wave response gradually declined over time. In the passive group, the ERG response was reduced at 3 weeks from the baseline and then remained relatively unchanged thereafter. At the end of the study (9 weeks from baseline) the ERG a-wave response of the passive group was similar to that of the control. In the active group, there was a significant reduction (P<0.05) in the ERG response at 3 weeks from the baseline and a further reduction in ERG response at weeks 7 and 9. The ERG responses at weeks 7 and 9 were significantly smaller than that of the control and passive groups (P<0.05).

The ERG response of the fellow (left) eye at various time points for the 3 study groups are shown in FIG. 18b. A marked reduction in the ERG a-wave amplitude at 3 weeks was noted in the passive and more so in the active group. However, the rate of change in the ERG a-wave amplitude for the control and active groups was similar after 3 weeks from the baseline. There was an increase in the ERG a-wave amplitude in the passive group at weeks 7 and 9. Inspection of the individual response from this group indicated that this increase in ERG a-wave response was driven by the data from the 2 animals. When these data were removed the average ERG a-wave amplitude of the passive group was similar to that of the control and active groups. This suggests that the apparent increase in the ERG a-wave response in the passive group at weeks 7 and 9 is likely to be outliers.

To further examine the safety and efficacy of 5 treatment sessions per week on photoreceptor function the ERG data were analysed by eye for each study group (FIGS. 19a to 19c). In the control group, the ERG responses of the 2 eyes were similar, except for the 3 week time point. In the passive group, the ERG responses of the right eye were similar to that of the control. The response from the left eye was generally greater than that of the right eye. The increase in the ERG response at weeks 7 and 9 were driven by the data from the 2 animals. When these data were excluded the average ERG response of the left eye at weeks 7 and 9 were similar to that of the right eye. In the active group, the ERG response of the right eye was significantly (p<0.05) smaller than that of the fellow (left) eye, particularly at weeks 3, 7 and 9. The ERG response of the right eye in the active group was also significantly (p<0.05) smaller than that of the other groups at ERG a-wave amplitude (μV).

The study indicated that stimulation treatment 5 times per week was associated with a small but significant reduction in the ERG a-wave response comparable to sham and naive controls. This initially indicated that the treatment regime of 1 hour per day, 5 days a week does not slow the photoreceptor degeneration in the P23His-3 model and that, in consideration of the previous study, treatment of less than 5 times a week, e.g. between about 1 and about 5 times a week, or between about 2 and 4 times a week could have been preferable. However, it has subsequently been identified that retinal trauma caused by the rat-specific nature of the experimental implant and surgery may have led to premature retinal degeneration and therefore a conclusion regarding maximum dosage interval cannot be drawn based on this particular study.

Example 3

Suprachoroidal therapeutic stimulation was tested on multiple human subjects using an implanted device including multiple implanted electrodes. After implantation, testing was carried out following a one-month period of recovery. Different combinations of electrodes positioned substantially beneath the retina, at the periphery of the retina, were tested to determine average charge activation thresholds where a visual percept was elicited in the patient, upon gradually increasing the charge levels. Thresholds were detected in a range of: charge: ~20-150 nC per electrode (or ~300 nC per pair of electrodes); charge density: ~7-50 $\mu C \cdot cm^2$ (platinum electrodes); rate: 50 pulses per second. Equivalent energy levels for different pulse rates can be inferred. The lower end of the charge range took into account the likelihood that early stage Retinitis Pigmentosa patients will have lower thresholds for activating their retinae.

Figure 31:
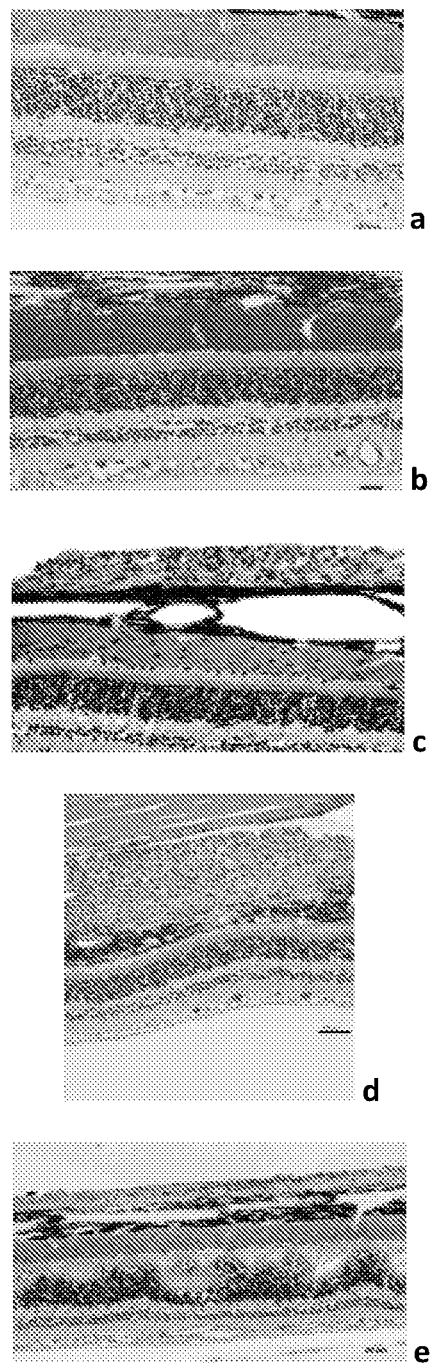
FIG. 31 shows, for a third example study, histological analysis of tissue layers for different levels of electrical stimuli (a-e).

An upper limit to charge levels was considered based on a normal-sighted cat model. With reference to FIG. 31, histopathology based indicators of stimulus-based injury and tissue reaction were considered for different electrical stimuli delivered to pairs of active electrodes as set forth in Table 1 below.

TABLE 1

| Histopathology | Stimulus | Tissue Reaction |
|---|---|---|
| a | <217 nC singles; ~50 pps; (*600 μm Ø) | Satisfactory |
| b | 500 nC per pair; 3 pairs; 50 pps | Satisfactory |
| c | 500 nC per pair; 6 pairs; 50 pps | Satisfactory |
| d | 580 nC per pair; 50 pps | Unsatisfactory |
| e | 930 nC per pair; 100 pps | Highly Unsatisfactory |

From this study, stimulus of: charge: ~250 nC per electrode (or 500 nC per pair of electrodes); charge density: ~90 μC·cm2 (platinum electrodes); and rate: 50 Pulses per pulses per second, can be determined as representing an example stimulation "limit", above which a risk of an acute or chronic inflammatory response, histiocytic changes or morphological changes, to the eye, resulting from the stimulation, becomes unacceptable. Equivalent energy levels for different pulse rates can be inferred.

Example 4

Figure 20:
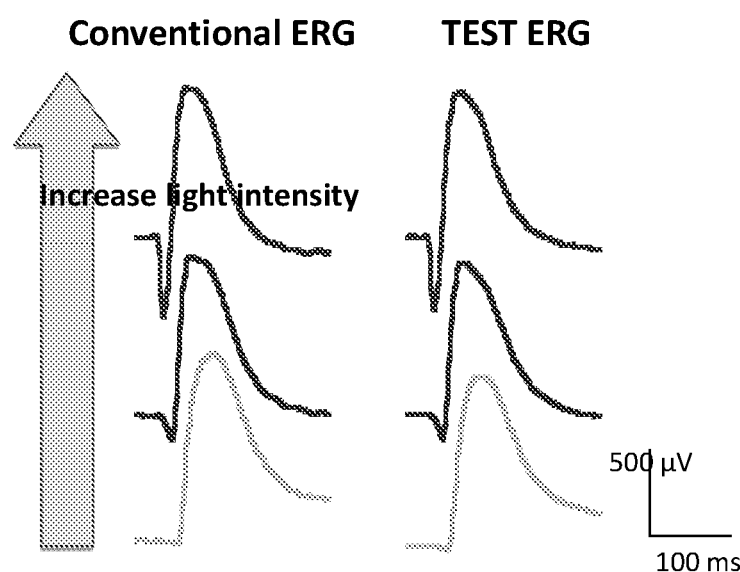
FIG. 20 shows, for a fourth example study, a comparison of electroretinograms using conventional ERG apparatus and using electrical apparatus according to the present disclosure.

Electrodes were suprachoroidally implanted in an eye to record full field flash evoked ERG responses. A comparison of this ("TEST") was made simultaneously with conventional ERG recordings employing corneal electrodes. With reference to FIG. 20, the implanted electrodes provided stable recordings over time, the recordings being longitudinally robust and less variable than conventional ERG.

Example 5

Normally-sighted adult cats (*Felis catus*) were surgically implanted with an implantable device comprising electrodes, and percutaneous cable, in their left suprachoroidal location. The implantable device included 5 platinum disc electrodes and was generally configured in accordance with the implantable device 7 described above with reference to FIGS. 10a to 10d, the electrodes being partially embedded within a flexible silicone substrate.

After wound healing, the subjects were assessed with clinical electroretinography (ERG). Recording of full-field ERG was performed using an Espion E2 system (Diagnosys LLC, Lowell, MA, USA) after 20 minutes of dark adaptation. ERG was recorded simultaneously from the implanted eye using (a) the implanted electrodes as the active input and (b) conventional, corneal-contact lens electrodes as the active input. A stainless-steel needle (Terumo 30 G) at the neck was used as the negative electrode for both the implanted and conventional set-ups and another grounding needle in the subject's flank.

The retinal responses to scotopic (dim) and photopic (bright) light flash luminance levels (0.01-10 $cd \cdot m^{-2}$) were recorded; however, only the combined rod-cone maximal ERG response (10 $cd \cdot m^{-2}$) is reported here as this ERG response provides information on the functional integrity of both the outer retina photoreceptors (a-wave) and mid retina bipolar cells (b-wave). The responses from both the implanted and conventional set-ups were cleaned and plotted according to ISCEV standards: international society for clinical electrophysiology of vision.

Figure 21A:
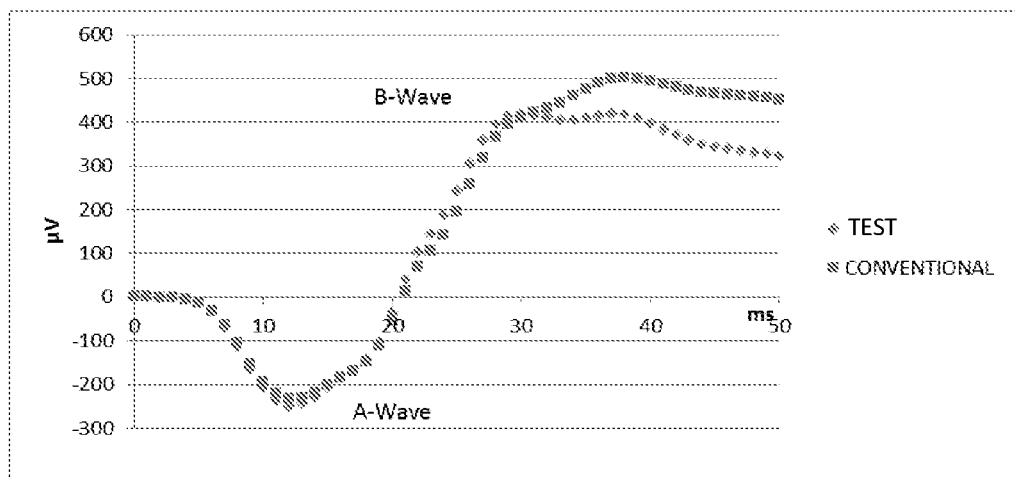
FIGS. 21a, 21b, and 21c show, for a fifth example study, a comparison of electroretinograms obtained using conventional ERG apparatus and using electrical apparatus ("TEST") according to the present disclosure in respective animal test subjects, either at single test points (FIG. 21a), two test points (FIG. 21b) or three test points (FIG. 21c).
Figure 21B:
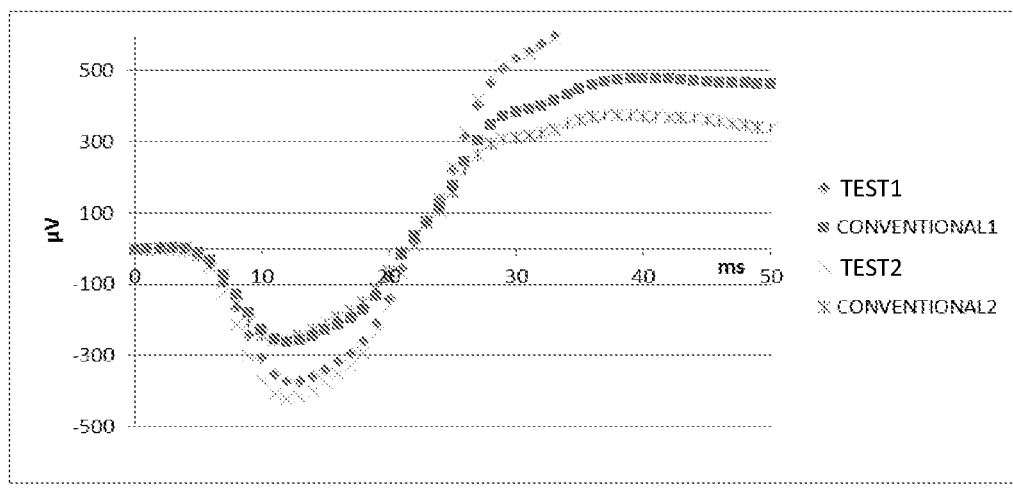
Figure 21C:
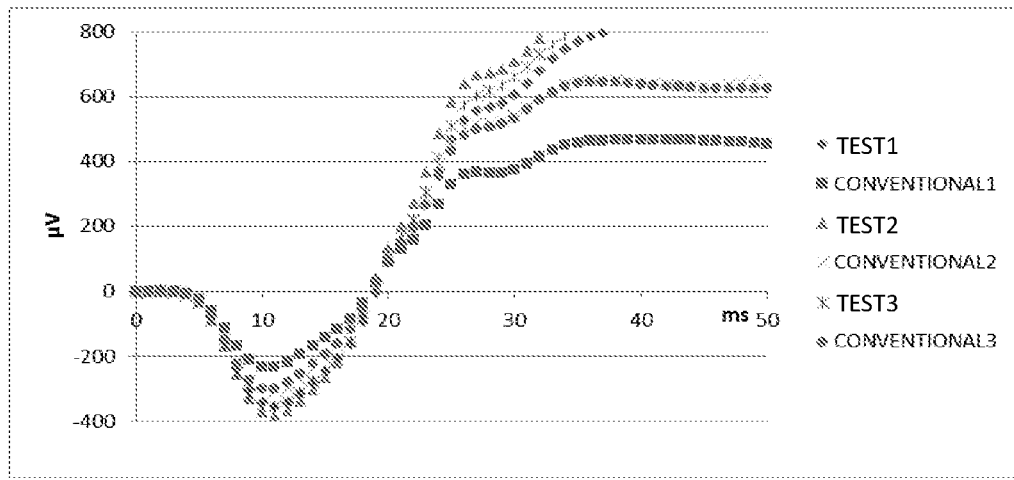

Referring to FIGS. 21a to 21c, which show raw data traces, use of the suprachoroidally implanted electrode apparatus according to the present disclosure provided increased (magnitude) amplitude for both the negative A-wave and the positive B-wave, in comparison to conventional corneal-contact lens electrode apparatus. The timing did not appear to be any different; this was expected as the location of the electrodes should not affect the signal latency based on the very small signal transmission distances.

Figure 22A:
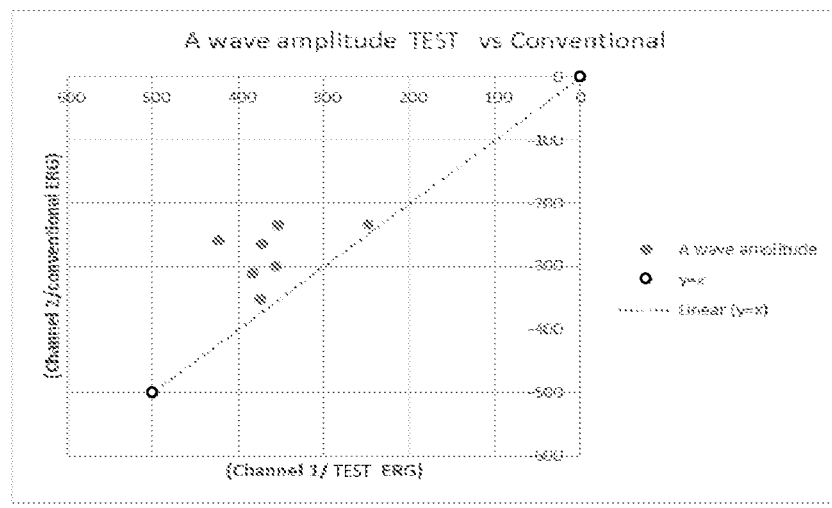
FIGS. 22a and 22b show, for the fifth example study, plots of A-wave and B-wave amplitudes, respectively, from electroretinograms obtained using conventional ERG apparatus and using electrical apparatus according to the present disclosure.
Figure 22B:
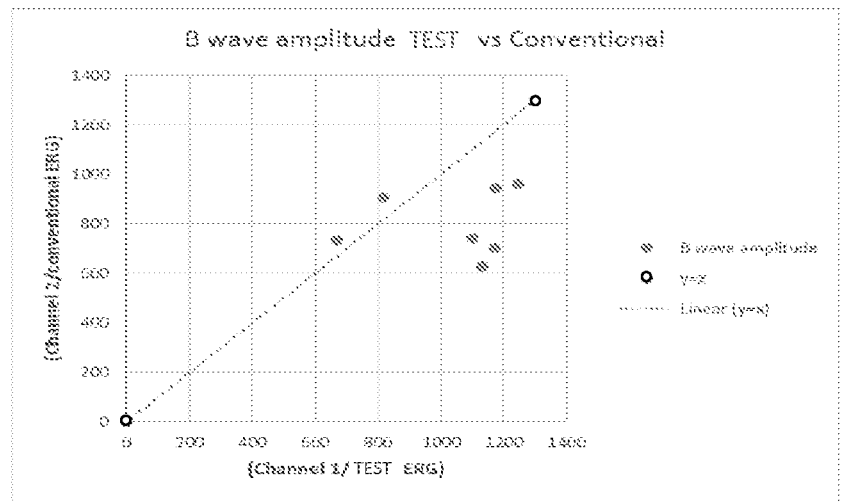

FIGS. 22a and 22b, which show cleaned amplitude and latency, also indicate that use of the apparatus according to the present disclosure provides increased (magnitude) amplitudes for both the negative A-wave and the positive B-wave, in comparison to the conventional apparatus. In addition, with the exception of one potential outlier in FIG. 22a and two potential outliers in FIG. 22b, it appears that the spread of responses along the amplitude dimension is lower for apparatus according to the present disclosure than for conventional apparatus.

Figure 23A:
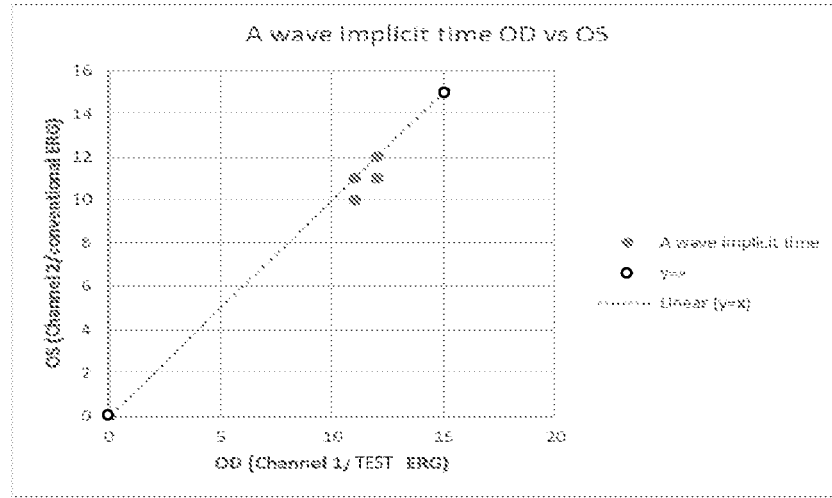
FIGS. 23a and 23b show, for the fifth example study, plots of A-wave latency (implicit time) and B-wave latency (implicit time), respectively, from electroretinograms obtained using conventional ERG apparatus and using electrical apparatus according to the present disclosure.
Figure 23B:
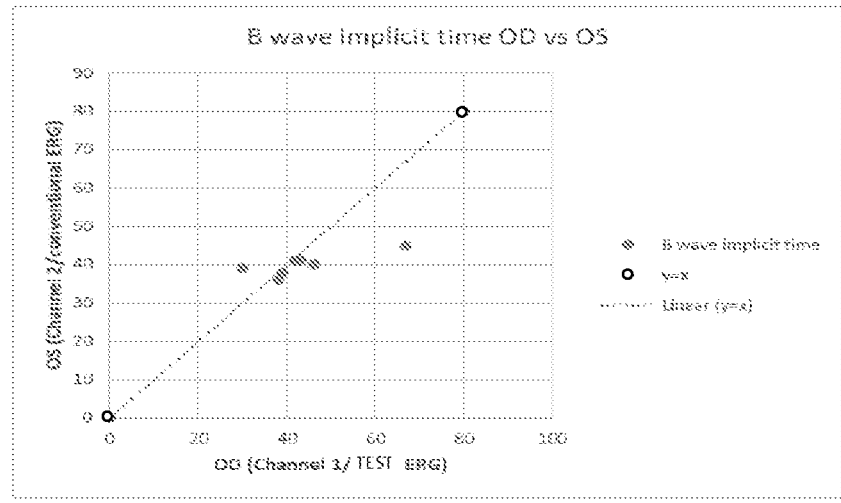

FIGS. 23a and 23b, which show A-wave latency (implicit time) and B-wave latency (implicit time), respectively, again indicate that use of the apparatus according to the present disclosure has no effect on timing of signals in comparison to the conventional apparatus.

Figure 24A:
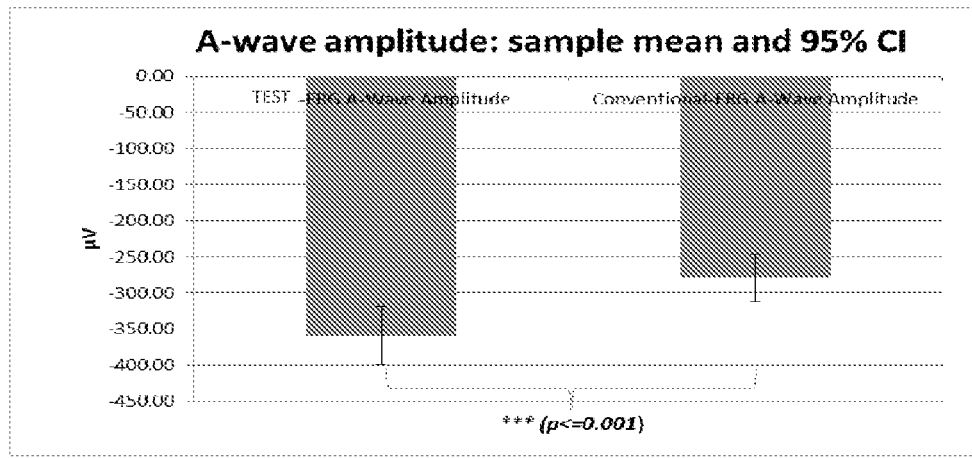
FIGS. 24a and 24b show, for the fifth example study, bar graphs comparing the means and 95% confidence intervals, of A-wave amplitude and B-wave amplitude measurements respectively, from electroretinograms obtained using conventional ERG apparatus and using electrical apparatus according to the present disclosure.
Figure 24B:
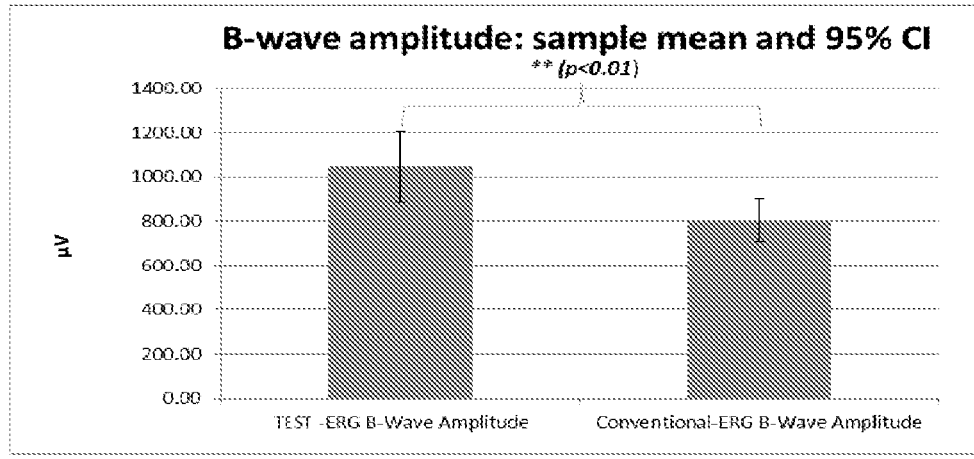

FIGS. 24a and 24b, which compare the means and 95% confidence intervals, of A-wave amplitude and B-wave amplitude measurements respectively, support the hypothesis that use of the apparatus according to the present disclosure provides no significant difference in signal latency.

Figure 25A:
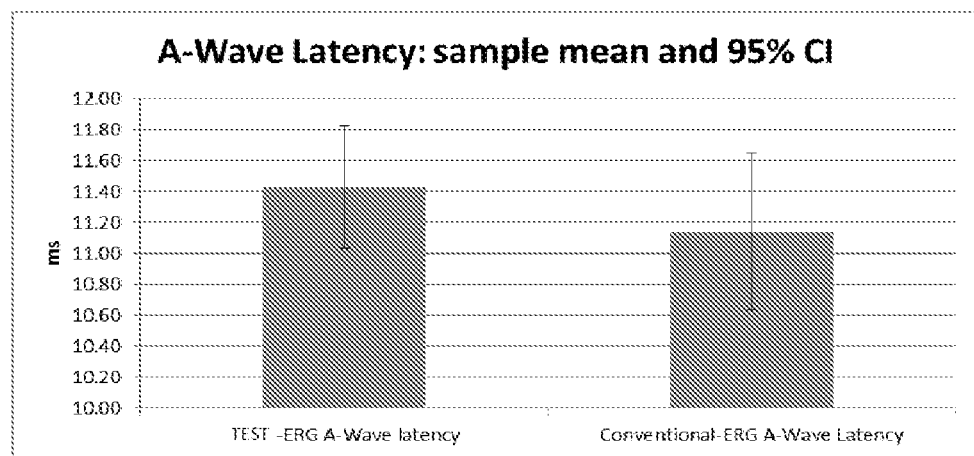
FIGS. 25a and 25b show, for the fifth example study, bar graphs comparing the means and 95% confidence intervals of A-wave latency (implicit time) and B-wave latency (implicit time) measurements, respectively, from electroretinograms obtained using conventional ERG apparatus and using electrical apparatus according to the present disclosure.
Figure 25B:
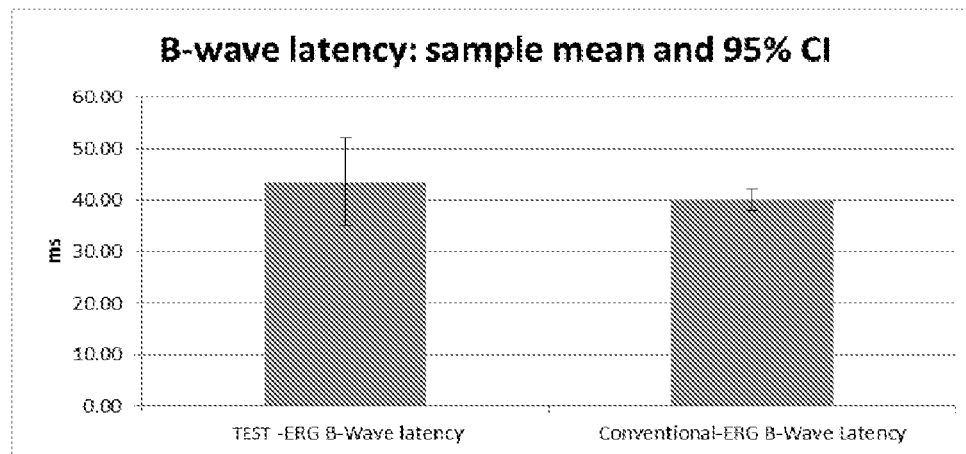

FIGS. 25a and 25b, which compare the means and 95% confidence intervals of A-wave latency (implicit time) and B-wave latency (implicit time) measurements respectively, support the hypothesis that use of from electroretinograms obtained using conventional ERG apparatus and using electrical apparatus according to the present disclosure.

The study indicated that the use of suprachoroidally implanted electrode apparatus provided for stronger ERG data than conventional corneal electrode apparatus, without affecting signal latency.

Example 6

ERG recordings were made using three different test variants: variant "A" in which a commercial ERG (Espion™) system was used, that employed a conventional contact lens electrode and conventional signal and delivery recording apparatus; variant "B" in which a suprachoroidally implanted electrode device according to the present disclosure was used (similar to the device illustrated in FIGS. 10a to 10d) in combination with the conventional (Espion™) signal and delivery recording apparatus; and variant "C" in which a suprachoroidally implanted electrode device according to the present disclosure was used (similar to the device illustrated in FIGS. 10a to 10d) in combination with signal and delivery recording apparatus according to the present disclosure (similar to the apparatus illustrated in FIG. 11b).

Figure 26A:
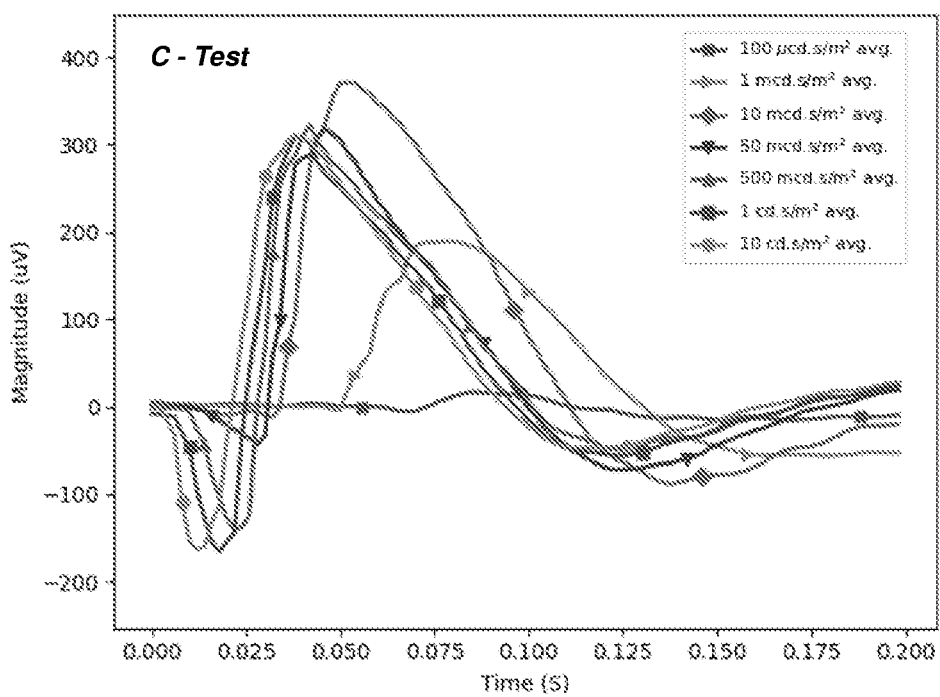
FIGS. 26a and 26b show, for a sixth example study, electroretinograms obtained using electrical apparatus according to the present disclosure and using entirely conventional ERG apparatus, respectively.
Figure 26B:
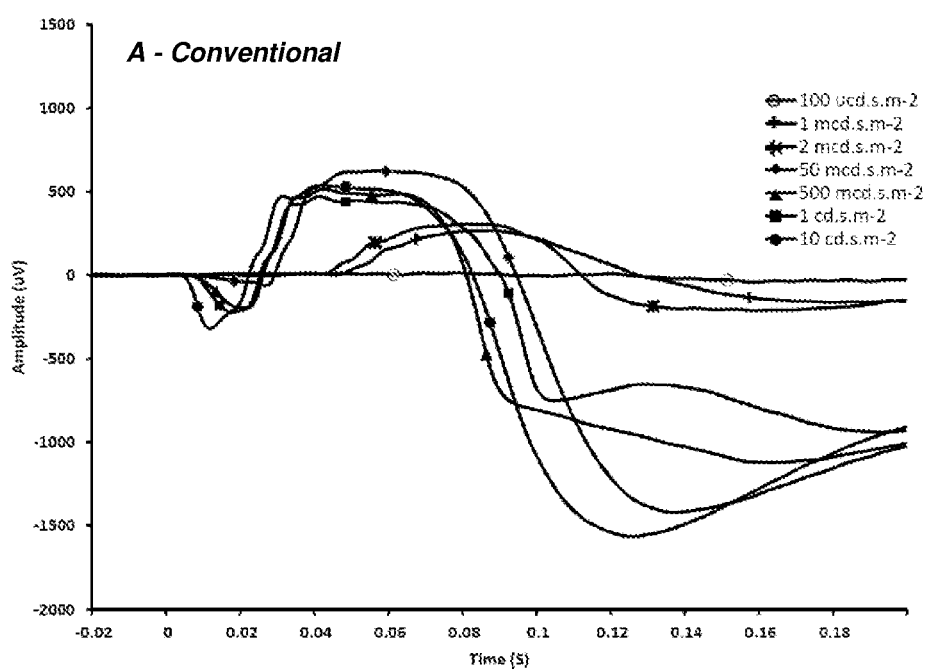

ERG waveforms recorded under variant C and variant A are illustrated in the graphs of FIGS. 26a and 26b, respectively. Under each variant, waveforms were recorded at different flash intensities (measured as average flash intensity in units of cd·s/m$^2$). The polarity of certain waveforms for variant C were inverted to enable comparison. The graphs show that there is generally increased waveform amplitude and decreased latency in peak signals at higher flash intensities. Moreover, this study shows that suprachoroidally implanted electrode apparatus provides for strong ERG data as per the conventional electrode apparatus, without affecting signal latency.

Figure 27:
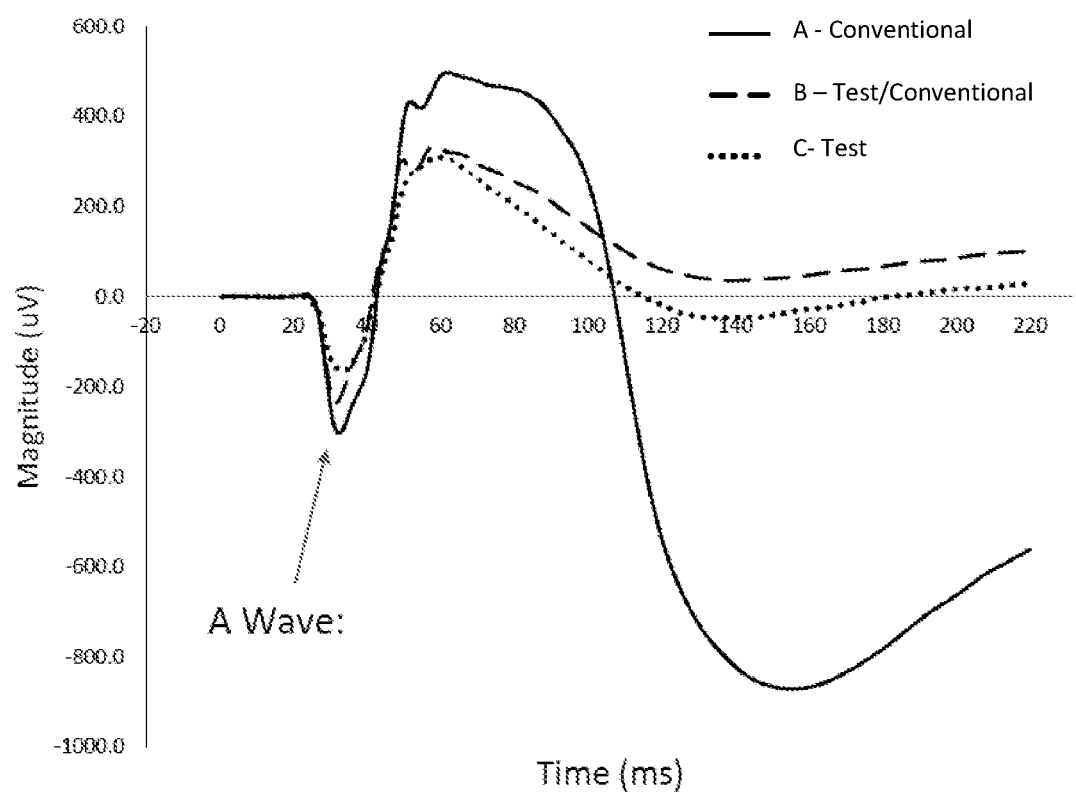
FIG. 27 shows, for the sixth example study, a comparison of electroretinograms obtained using conventional ERG apparatus and using electrical apparatus according to the present disclosure.

ERG waveforms recorded under variant A, B and C are illustrated in the graph of FIG. 27. For each variant, waveforms were recorded at the same flash intensity. The polarity of waveforms for variants B and C were inverted to enable comparison. In this instance, while there is a difference in amplitude between the waveforms, it was considered attributable to filter settings of the recording apparatus used.

Figure 28A:
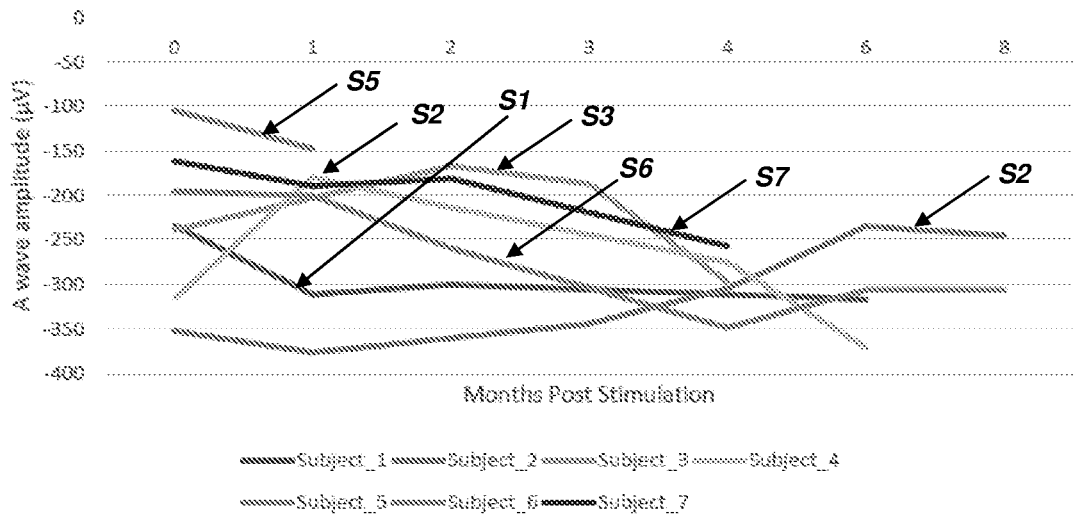
FIGS. 28a and 28b show, for the sixth example study, a comparison of A-wave amplitudes obtained successively 1-month apart, for different patients, using conventional ERG apparatus (FIG. 28a) and using electrical apparatus according to the present disclosure (FIG. 28b)
Figure 28B:
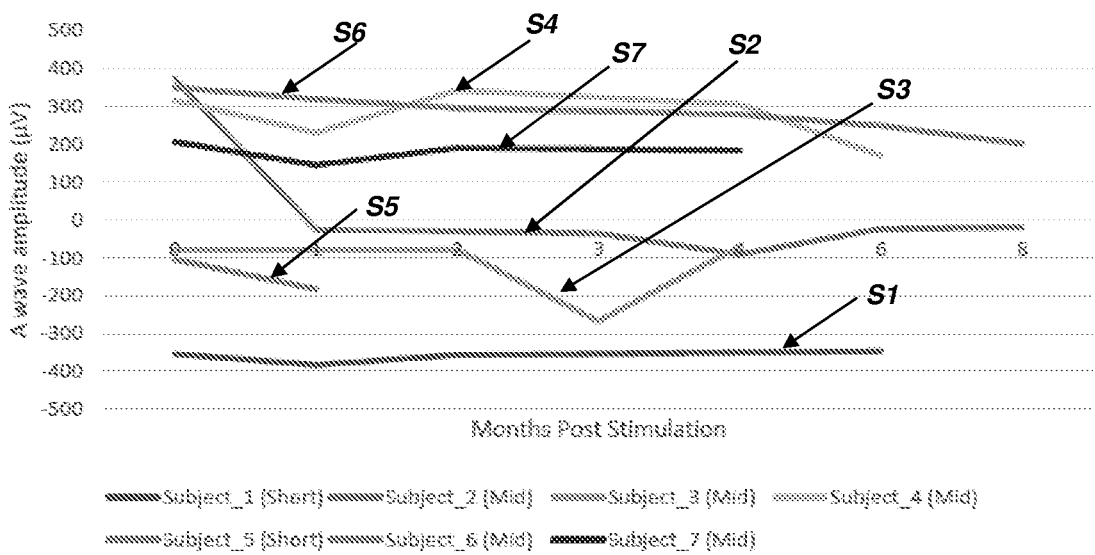

FIGS. 28a and 28b show, respectively, A-wave amplitudes from ERG recordings obtained using the commercially available system (variant A; FIG. 28a) and using apparatus according to the present disclosure (variant B; FIG. 28b). Recordings were taken after successive 1-month periods and from seven different subjects.

Under variant B, subjects 1 and 5 (S1, S5) were implanted with a relatively short implantable device ("short device"; approximately 8.9 mm long), with three ganged active electrodes of the implantable device being positioned at a distance of about 7.5 mm distally from the proximal end of the implantable device and about 10.5 mm from the limbus. Under variant B, subjects 2, 3, 4, 6 and 7 (S2, S3, S4, S6, S7) were implanted with a relatively long implantable device ("mid device", approximately 11.35 mm long), with three ganged active electrodes of the implantable device being positioned at a distance of about 10 mm distally from the proximal end of the implantable device and about 13 mm from the limbus. As a result, the active electrodes for subjects 2, 3, 4, 6 and 7 were located at the periphery of the retina, and closer to the central retina (beneath the retina without infringing on the central retina) in comparison to the active electrodes for subjects 1 and 5.

The graphs of FIGS. 28a and 28b indicate that, following an initial settling period, ERG recordings used apparatus according to the present disclosure (variant B) are more consistent than those made with conventional contact lens electrodes (variant A). Notably, the recordings were all made in normal-sighted subjects with no expected photoreceptor deterioration.

The graph of FIG. 28b also indicates that different locations of the implanted electrodes give rise to different polarities in the ERG recordings, including the A-wave peaks. This was also evident from the inversions required to ERG waveforms present in graphs as discussed above. For the subjects implanted with the "mid device", having electrodes beneath the retina, more positive A-wave amplitudes are seen while, for the subjects implanted with the "short device", having electrodes spaced further from the retina, more negative A-wave amplitudes are seen.

For subject 2 (S2), there was some initial array movement during the settling period (when the active electrodes were located closer to the incision). However, for subject 2, the ERG amplitude became negative at subsequent 1-month periods. This is consistent with the hypothesis that there is a relationship between the Anterior-Posterior location of the tip of the implantable device and the waveform polarity. Post 1-month implantation, in the ultimate resting location of subject 2's implantable device, the electrodes would have been close to the threshold position of polarity inversion and thus the resulting vector-summation of the A-wave amplitude was closer to zero. The ERG waveform is the summation of the retina's neural activity. The polarity of the waveform shifts from the "normal" state (that which is obtained using a conventional corneal contact lens recording electrode as the positive terminal) to an "inverted" state as the recording site is advanced posteriorly (behind the retina). A "normal" polarity waveform is characterised by an A-wave with a negative amplitude. As indicated, the "short devices" returned "normal" polarity waveforms, but the "mid devices" returned "inverted polarity" waveforms.

In view of the Example 6 study it is identified herein that methods and apparatus according to the present disclosure may assist in a surgical procedure, e.g. to assist in identifying when one or more implanted electrodes have reached a desired location in the eye relative to the retina, e.g. when they have reached a positioned behind the retina, which may be a desirable position to monitor ERG recordings and/or deliver stimulation to the retina or otherwise. In some embodiments, the location of the one or more electrodes may be determined substantially in real time during a surgical procedure. Additionally or alternatively, in some embodiments the methods and apparatus may be used to identify if the one or more electrodes have moved, e.g. undesirably, from an intended implantable location relative to the retina, e.g. moved away from a position behind the retina. Such movement may occur over a period of time after initial surgical implantation and the methods and apparatus according to the present disclosure may therefore provide a means for detection of such movement.

In some embodiments, the determining of the location, or a change in location, of the one or more electrodes relative to the retina of the eye may also be based on amplitude of the ERG signal. When the amplitude is identified as relatively low or lower than amplitudes of other ERG signals, for example, it may be determined that the one or more electrodes are located at a position close to or closer to a threshold location for polarity inversion (the lower amplitude resulting from a vector-summation of different polarity amplitudes).

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An electrical stimulation apparatus for delivering therapeutic electrical stimulation to an eye of a patient, the apparatus comprising:
   an implantable device comprising:
      an elongate substrate having a distal end and a proximal end, wherein a length of the substrate in a longitudinal direction of the substrate extending between the distal and proximal ends of the substrate is between 5 mm and 15 mm; and
      one or more electrodes located in or on the substrate, the electrodes configured for delivering therapeutic electrical stimulation to the eye, the implantable device being configured for implanting in a suprachoroidal space between the sclera and choroid layers of the eye;
      wherein, when implanted, one or more distal-most electrodes of the one or more electrodes is located at a position beneath the retina of the eye, the substrate is not positioned beneath, and the one or more electrodes do not infringe on the central retina of the eye; and
   a controller configured to control a delivery of therapeutic electrical stimulation to the eye using the one or more electrodes,
   wherein the therapeutic electrical stimulation prevents or slows degradation of visual function of the eye.

2. The apparatus of claim 1, wherein the therapeutic electric stimulation is delivered at a current of about 50 to 150 µA, 0.5 to 200 pulses per second, and optionally at a minimum charge level of between 20 nC to 150 nC at 50 pulses per second and a maximum charge level of about 250 nC at 50 pulses per second.

3. The apparatus of claim 1, wherein:
   the therapeutic electric stimulation is delivered for one or more sessions, each session being about 15 minutes to about 2 hours long, and/or
   sessions of the therapeutic electric stimulation are delivered 1 time to about 4 or about 5 times per week, and/or
   the therapeutic electrical stimulation is delivered at a current of about 100 µA, 1 pulse per second, for 1 hour about 2 times per week, for at least 4 weeks.

4. The apparatus of claim 1, further comprising a plurality of the electrodes.

5. The apparatus of claim 1, wherein the substrate is flexible and comprises a polymeric material, the electrodes being at least partly embedded in the polymeric material.

6. The apparatus of claim 5, wherein the substrate has a proximal end, a first side, a second side, and first and second opposite surfaces each extending between the distal and proximal ends and the first and second sides, wherein the electrodes are exposed at one or both of the first and second surfaces, and wherein the substrate is configured for insertion, via an incision in the eye, distal end first, to a stimulation position between the sclera and choroid layers.

7. The apparatus of claim 6, further comprising a plurality of the electrodes, wherein the electrodes are positioned at different sides of a longitudinal centre line of the substrate that extends between the proximal and distal ends of the substrate and not one of the electrodes extends across the longitudinal central line of the substrate.

8. The apparatus of claim 6, further comprising a plurality of the electrodes, wherein the electrodes are arranged in a staggered pattern.

9. The apparatus of claim 6, wherein the electrodes are aligned in one or more rows extending in a longitudinal direction of the substrate between the distal and proximal ends of the substrate, but not aligned in columns extending in a transverse direction of the substrate.

10. The apparatus of claim 6, wherein:
   the length of the substrate is between 5 mm and 13 mm, 7 mm and 13 mm, 7 mm and 11 mm, 7 mm and 12 mm, 9 mm and 11 mm, 9 mm and 12 mm, 10 mm and 12 mm, or 11 mm and 12 mm, and
   a width of the substrate, in a transverse direction of the substrate extending between the first and second sides of the substrate, is between 3 mm and 7 mm, 3 mm and 6 mm, 4 mm and 6 mm, or 4 mm and 5 mm or 5 mm and 7 mm.

11. The apparatus of claim 6, wherein each of the one or more electrodes has an exposed area between 0.2 mm$^2$ and 7.1 mm$^2$, 0.8 mm$^2$ and 7.1 mm$^2$, 1.7 mm$^2$ and 7.1 mm$^2$, or 1.7 mm$^2$ and 4.9 mm$^2$.

12. The apparatus of claim 6, wherein the distance between the distal-most electrode for delivering therapeutic electrical stimulation to the eye and the proximal end of the substrate is between about 7 mm and 12 mm, 8 mm and 11 mm, 9 mm and 11 mm, or about 10 mm.

13. The apparatus of claim 1, wherein the implantable device is configured such that the distance between the distal-most electrode for delivering therapeutic electrical stimulation to the eye and the limbus of the eye, when the device is implanted in the eye, is between about 10 mm and 15 mm, 11 mm and 14 mm, 12 mm and 14 mm, or about 13 mm.

14. The apparatus of claim 1, further comprising a lead through which conductors extend from the implantable device, the conductors being connected to the one or more electrodes, the lead being configured to extend through an incision in the surface of the eye to enable electrical communication between the implantable device and one or more extra-ocular devices.

15. The apparatus of claim 14, wherein a distance between the one or more distal-most electrodes of the implantable device and a point at which the lead extends from the substrate is between about 5 mm and about 10 mm, between about 6 mm and about 9 mm, between about 7 mm and about 9 mm, or about 8 mm.

16. A method of delivering therapy to an eye of a patient, comprising:
implanting an implantable device through an incision in the surface of the eye and distally towards a retina of the eye in a suprachoroidal space between the sclera and choroid layers of the eye, the implantable device comprising:
an elongate substrate having a distal end and a proximal end, wherein a length of the substrate in a longitudinal direction of the substrate extending between the distal and proximal ends of the substrate is between 5 mm and 15 mm; and
one or more electrodes in or on the substrate, wherein, when implanted, one or more distal-most electrodes of the one or more electrodes is located at a position beneath the retina of the eye, the substrate is not positioned beneath, and the one or more electrodes do not infringe on the central retina of the eye; and
delivering therapeutic electrical stimulation to the eye using the one or more electrodes comprised in the implantable device,
wherein the therapeutic electrical stimulation prevents or slows degradation of visual function of the eye.

17. The method of claim 16, comprising implanting the implantable device at a position corresponding to a temporal area of the retina.

18. The method of claim 16, wherein the therapeutic stimulation provides therapy to a portion of the eye that is not in contact with the one or more electrodes delivering the electrical stimulation.

19. The method of claim 16, wherein the method protects against retinal degeneration of the eye or photoreceptor loss in the eye.

20. The method of claim 16, the method further comprising making the incision in the surface of the eye beneath a lateral rectus muscle of the eye.

* * * * *